US007818185B2

(12) United States Patent
Bjorner et al.

(10) Patent No.: US 7,818,185 B2
(45) Date of Patent: Oct. 19, 2010

(54) METHOD, SYSTEM AND MEDIUM FOR ASSESSING THE IMPACT OF VARIOUS AILMENTS ON HEALTH RELATED QUALITY OF LIFE

(75) Inventors: Jakob B. Bjorner, Charlottenlund (DK); John E. Ware, Medford, MA (US); Mark R. Kosinski, Sterling, MA (US); Barbara Sardinha, Portsmouth, RI (US); James E. Dewey, Narragansett, RI (US)

(73) Assignee: Qualitymetric Incorporated, Lincoln, RI (US)

( * ) Notice: Subject to any disclaimer, the term of this patent is extended or adjusted under 35 U.S.C. 154(b) by 1253 days.

(21) Appl. No.: 11/377,773

(22) Filed: Mar. 15, 2006

(65) Prior Publication Data
US 2006/0218007 A1 Sep. 28, 2006

Related U.S. Application Data

(63) Continuation-in-part of application No. 09/873,500, filed on Jun. 4, 2001.

(60) Provisional application No. 60/209,105, filed on Jun. 2, 2000, provisional application No. 60/662,060, filed on Mar. 15, 2005.

(51) Int. Cl.
*A61B 5/00* (2006.01)
*G06F 19/00* (2006.01)

(52) U.S. Cl. .................... 705/3; 705/2; 705/4; 434/236; 434/322

(58) Field of Classification Search .................. 434/236, 434/322
See application file for complete search history.

(56) References Cited

OTHER PUBLICATIONS

Ware, Jr., John E., Jakob Bjorner, and Mark Kosinski, Dynamic Health Assessments: The Search for More Practical and More Precise Outcomes Measures, The Quality of Life Newsletter, Jan. 1999-Apr. 1999.*
Schlenk et al., "Health-related quality of life in chronic disorders: a comparison across studies using the MOS SF-36," Quality of Life Research, 7:57-65 (1998).*
Bayliss MS, Dewey JE, Dunlap I, Batenhorst AS, Cady R, Diamond ML et al. (2003). A study of the feasibility of Internet administration of a computerized health survey: the headache impact test (HIT). Qual.Life Res, 12, 953-961.
Bergner M, Bobbitt RA, Kressel S, Pollard WE, Gilson BS, & Morris JR (1976). The sickness impact profile: conceptual formulation and methodology for the development of a health status measure. Int. J Health Serv., 6, 393-415.
Bjorner JB, Kosinski M, & Ware JE, Jr. (2003a). Calibration of an item pool for assessing the burden of headaches: an application of item response theory to the headache impact test (HIT). Qual Life Res, 12, 913-933.
Bjorner JB, Kosinski M, & Ware JE, Jr. (2003b). The feasibility of applying item response theory to measures of migraine impact: a re-analysis of three clinical studies. Qual Life Res, 12, 887-902.

(Continued)

*Primary Examiner*—Gerald J. O'Connor
*Assistant Examiner*—Linh Michelle Le
(74) *Attorney, Agent, or Firm*—Fulbright & Jaworski LLP

(57) ABSTRACT

The present invention relates to a system and method for assessing the impact of an ailment on a health related quality of life domain of a patient using a standardized common metric. The standardized common metric of the present invention enables the impact of various ailments to be compared.

31 Claims, 5 Drawing Sheets

OTHER PUBLICATIONS

Bjorner JB, Kosinski M, & Ware JE, Jr. (2003c). Using item response theory to calibrate the Headache Impact Test (HIT) to the metric of traditional headache scales. Qual Life Res, 12, 981-1002.

Bjorner JB & Ware JE, Jr. (1998). Using Modern Psychometric Methods to Measure Health Outcomes. Medical Outcomes Trust Monitor, 3, 12-16.

Bombardier C, Melfi CA, Paul J, Green R, Hawker G, Wright J et al. (1995). Comparison of a generic and a disease-specific measure of pain and physical function after knee replacement surgery. Med. Care, 33, AS131-AS144.

Custers JW, Hoijtink H, van der NJ, & Helders PJ (2000). Cultural differences in functional status measurement: analyses of person fit according to the Rasch model. Qual.Life Res, 9, 571-578.

Deyo RA & Patrick DL (1989). Barriers to the use of health status measures in clinical investigation, patient care, and policy research. Med. Care, 27, S254-S268.

Drasgow F, Levine MV, & Williams EA (1985). Appropriateness measurement with polychotomous item response models and standardized indices. Br Journal of Math Stat Psychol, 38, 67-86.

Essink-Bot ML, Krabbe PF, Bonsel GJ, & Aaronson NK (1997). An empirical comparison of four generic health status measures. The Nottingham Health Profile, the Medical Outcomes Study 36-item Short-Form Health Survey, the COOP/WONCA charts, and the EuroQol instrument. Med Care, 35, 522-537.

Gandek, B., Alacoque, J., Uzun, V., Andrew-Hobbs, M., & Davis, K. Translating the Short-Form Headache Impact Test (HIT-6) in 27 Countries: Methodological and Conceptual Issues. Qual Life Res, (in press).

Kantz ME, Harris WJ, Levitsky K, Ware JE, Jr., & Davies AR (1992). Methods for assessing condition-specific and generic functional status outcomes after total knee replacement. Med Care, 30, MS240-MS252.

Kosinski M, Bayliss MS, Bjorner JB, Ware JE, Jr., Garber WH, Batenhorst A et al. (2003a). A six-item short-form survey for measuring headache impact: the HIT-6. Qual Life Res, 12, 963-974.

Kosinski M, Bjorner JB, Ware JE, Jr., Batenhorst A, & Cady RK (2003b). The responsiveness of headache impact scales scored using 'classical' and 'modern' psychometric methods: a re-analysis of three clinical trials. Qual Life Res, 12, 903-912.

McHorney CA (1997). Generic health measurement: past accomplishments and a measurement paradigm for the 21$^{st}$ century. Ann Intern Med, 127, 743-750.

Patrick DL & Deyo RA (1989). Generic and disease-specific measures in assessing health status and quality of life. Med.Care, 27, S217-S232.

Patrick DL & Erickson P (1988). Assessing health-related quality of life for clinical decision-making. In Walker S (Ed.), Quality of life: assessment and application (pp. 9-49). London: MTP Press.

Stewart AL, Greenfield S, Hays RD, Wells K, Rogers WH, Berry SD et al. (1989). Functional status and well-being of patients with chronic conditions. Results from the Medical Outcomes Study [published erratum appears in JAMA Nov. 10, 1989;262(18):2542]. JAMA, 262, 907-913.

Tarlov AR, Ware JE, Jr., Greenfield S, Nelson EC, Perrin E, & Zubkoff M (1989). The Medical Outcomes Study. An application of methods for monitoring the results of medical care. JAMA, 262, 925-930.

Thissen D, Steinberg L, & Wainer H (1993). Detection of Differential Item Functioning Using the Parameters of Item Response Models. In Holland PW & Wainer H (Eds.), Differential Item Functioning (pp. 67-113). Hillsdale NJ: Lawrence Erlbaum Ass.

Ware JE, Jr. (1995). The Status of Health Assessment 1994. Annu Rev Public Health, 16, 327-354.

Ware JE, Jr. (2003). Conceptualization and measurement of health-related quality of life: comments on an evolving field. Arch.Phys. Med.Rehabil., 84, S43-S51.

Ware JE, Jr., Bjorner JB, & Kosinski M (2000). Practical implications of item response theory and computerized adaptive testing: a brief summary of ongoing studies of widely used headache impact scales. Med.Care, 38, II73-II82.

Ware JE, Jr., Kosinski M, Bayliss MS, McHorney CA, Rogers WH, & Raczek A (1995). Comparison of methods for the scoring and statistical analysis of SF-36 health profile and summary measures: summary of results from the Medical Outcomes Study. Med Care, 33, AS264-79.

Ware JE, Jr., Kosinski M, Bjorner JB, Bayliss MS, Batenhorst A, Dahlof CG et al. (2003). Applications of computerized adaptive testing (CAT) to the assessment of headache impact. Qual Life Res, 12, 935-952.

Warm TA (1989). Weighted likelihood estimation of ability in item response theory. Psychometrika, 54, 427-450.

Wilson IB & Cleary PD (1995). Linking clinical variables with health-related quality of life. A conceptual model of patient outcomes. JAMA, 273, 59-65.

Muraki E. A Generalized Partial Credit Model. In van der Linden WJ, Hambleton RK, eds. Handbook of Modern Item Response Theory, pp. 153-64. Berlin: Springer, 1997.

Apolone et al., "Health-related quality of life (HRQOL) and migraine," J. Headache Pain, vol. 2: S21-S24, (2001).

Shafazand et al., "Health-related quality of life in patients with pulmonary arterial hypertension," Chest., vol. 126:1452-1459 (2004).

* cited by examiner

Example of functions:
Emotional, social, and role

Least  Restrict recreational activities
severe Lie down and rest
        Feel frustrated
        Difficult to focus attention
        *Feel irritable*
        Limit ability to do activities
        Difficulty in performing daily activities
        Keep from enjoying social activities
        Limit ability to concentrate
        Keep you from socializing
        Afraid of letting others down
        Avoid social or family activities
        Place stress on the relationships
        Feel like a burden on others
        Avoid traveling
        Feel desperate
        Cancel work or daily activities
Most  Need help in routine daily tasks
severe Keep you in bed

Examples of conditions

Least  Hernia
severe *Rhinitis*
        Asthma
        Overweight
        Osteoarthritis
        Diabetes
        Chronic Obstructive Pulmonary
          Disease
        Depression
Most  Congestive Heart Failure
severe Rheumatoid Arthritis Disease Impact Item:
*In the past 4 weeks,
how much of the time did you feel
irritable because of your rhinitis?*

FIG. 1

Item 1

Item 2

Population distribution

METHOD, SYSTEM AND MEDIUM FOR ASSESSING THE IMPACT OF VARIOUS AILMENTS ON HEALTH RELATED QUALITY OF LIFE

RELATED APPLICATION

The present application claims benefit of U.S. Provisional Application No. 60/662,060 filed Mar. 15, 2005, and the present application is a continuation-in-part of U.S. application Ser. No. 09/873,500, filed Jun. 4, 2001, which is a continuation in-part of U.S. Provisional Application Ser. No. 60/209,105 filed Jun. 2, 2000, which are all incorporated by reference in their entireties.

BACKGROUND OF THE INVENTION

The present invention relates to an assessment technique, which is conveniently practiced on a computer. The computer is either a 'stand alone' or connected to a computer network, such as a local area network (LAN) or the world wide web, which is frequently and interchangeably referred to as the Internet. Other devices, including wireless enabled devices, may also be utilized in the assessment technique. Specifically, the present invention relates to a system, method and medium for the assessment of the impact of an ailment on a health related quality of life domain of a patient, where a standardized common metric for comparing the impact of various ailments is established.

In the United States alone, over 100 million people have chronic health conditions, accounting for an estimated $700 billion in annual medical costs. In an effort to control these medical costs, many healthcare providers have initiated outpatient or home healthcare programs for their patients. The potential benefits of these programs are particularly great for chronically ill patients who must treat their diseases on a daily basis. However, the success of these programs is dependent upon the ability of the healthcare providers to monitor their patients remotely in order to avert medical problems before they become complicated and costly.

Various surveys for assessing health and impact of a particular disease are available, but there is no standardized common metric for comparing the impact of various ailments. Although the disease-specific tools, aimed at assessing the impact of a particular disease on HRQOL, have certain sensitivity and specificity aspects, unfortunately they do not possess the ability to compare results across diseases. This inability makes it harder to build a body of results that could help interpretation of the meaning of specific scores.

*SF-36 Health Survey—Manual & Interpretation Guide*, written by John H. Ware, Jr., Ph.D. et al., and published by The Health Institute, New England Medical Center, Boston, Mass. (copyright, 1993) describes a protocol for an improved health assessment and evaluation technique. The guide includes a thirty-six question survey, which is useful in assessing general health variables. Many have cited the thirty-six question survey as providing excellent results notwithstanding its brevity as compared to other surveys.

"Dynamic Health Assessments: The Search for More Practical and More Precise Outcomes Measures" by John E. Ware, Jr., Jakob Bjorner and Mark Kosinski, (inventors of the present application) published in the *Quality of Life* newsletter, No. 21 (January-April 1999) generally discusses a psychometric method for assessing indicia of ideal health status.

An article related to the SF-36 survey is "The MOS 36-Item Short Form Health Survey (SF-36)" by John H Ware Jr., PhD. and Cathy Donald Shelbourne, PhD, published in *Medical Care*, Vol. 30, No. 6, June 1992.

A further article related to certain computer testing algorithms is described at pages 103-135 of *Computer Adaptive Testing—A Primer* by Howard Wainer, et al. published by Lawrence Erlbaum Associates, Hillsdale, N.J. 1990.

A further shortcoming in these surveys is that they are often directed towards providing an objective evaluation of a patient and his/her health. This method of evaluation doesn't allow a patient to provide their own feedback as to their own perceived state of health, which can be a significant distinction. Although, the objective evaluation of the patient and his/her health provides the healthcare practitioner or healthcare provider with objective indicia as to the perceived state of the patient's health, it is not necessarily helpful in all instances to the patient in understanding his/her health status or progress during any particular time interval. That is, the objective survey results are not frequently presented in a meaningful fashion to the patient. Rather, many of these surveys are primarily directed to the healthcare provider or healthcare organization. A subjective survey is much more meaningful to the patient in understanding their own health status and progress over any time interval. Healthcare providers/healthcare organizations, however, rarely utilize such subjective surveys, and traditionally favor the objective types of surveys known to the art.

Another shortcoming relating to the systems, methods, and surveys, which are cited above, is the relevant inflexibility of the surveys, which are set out in a standardized form and need to be completed in total by the patient/respondent every time that the survey is taken. Thus, patient/respondent encounters the same burden every time that he or she responds to such survey.

Furthermore, the prior art tests and surveys are non-adaptive. Prior survey results of a patient/respondent, or a group of patients/respondents, do not affect the future surveys that they are given. As such, the later surveys do not provide for differentiation in the health status of a patient.

An additional problem in the prior art surveys is their inflexible modes of administration. The surveys generally consist of either the traditional paper-based type or a computer-based replica of the same. The traditional paper-based versions provide a series of questions on paper sheets or booklets for the patient/respondent. After the patient/respondent completes the survey, the administrators evaluate the responses. While cost effective, the format remains inflexible. In the case of the computer-based surveys, many of the prior art surveys are little more than computer-driven versions of the same paper-based surveys, which provide little or nothing in added flexibility.

A further shortcoming in many of the prior art surveys is that they are unsuited for self-administration by a patient/respondent. In the context of the objective surveys described above, the patient/respondent may be very capable of taking the survey and responding to the questions provided therein, but many of these surveys do not provide an immediate response that is readily understood by the patient/respondent by the conclusion of the survey. Thus, while the "objective" type survey may provide meaningful results to a medical practitioner or a health services organization, it is not particularly adapted as a self-monitoring instrument to a patient or respondent.

Additionally, Related art includes tools for assessing Health Related Quality of Life (HRQOL) which have enabled researchers and clinicians to better understand the impact of disease from the patient's perspective (Ware J E, Jr. (2003). Conceptualization and measurement of health-related quality of life: comments on an evolving field. *Arch.Phys.Med.Rehabil.,* 84, S43- S51; and McHorney CA (1997). Generic health measurement: past accomplishments and a measurement paradigm for the 21st century. *Ann Intern Med,* 127, 743-750, which are incorporated herein by reference in their entirety). Such understanding is particularly important for the treatment of chronic diseases prevalent in the aging population. Evaluating the impact of disease on the HRQOL of the elderly person, for example, is a key element in treatment evaluation, monitoring of patients and screening for potential problems.

Such evaluation of the impact of disease on HRQOL has been performed with two distinct sets of questionnaires: generic and disease-specific. In general, disease-specific measures demonstrate greater sensitivity (Kantz M E, Harris W J, Levitsky K, Ware J E, Jr., & Davies A R (1992). Methods for assessing condition-specific and generic functional status outcomes after total knee replacement. *Med Care,* 30, MS240-MS252; and Bombardier C, Melfi C A, Paul J, Green R, Hawker G, Wright J et al. (1995). Comparison of a generic and a disease-specific measure of pain and physical function after knee replacement surgery. Med. Care, 33, AS 131-AS 144, which are incorporated herein by reference in their entirety) and specificity than generic measures (Kantz et al., 1992) while generic measures better capture the total burden of disease (Ware J E, Jr. (1995). The Status of Health Assessment 1994. *Annu Rev Public Health,* 16, 327-354, which is incorporated herein by reference in its entirety; Bombardier et al., 1995). In the presence of comorbid conditions, generic measures reflect the combined effects of primary and comorbid conditions, whereas disease-specific measures reflect mainly the primary disease (Kantz et al., 1992). Further, generic questionnaires can be used with different diseases and thus allow comparison of disease burden across diseases. Thus, when assessing patients the researcher or clinician needed to use both types of questionnaires or had to make a choice between the generalizability of the generic questionnaire and the sensitivity and specificity of the disease-specific questionnaire.

Therefore, it is desirable to have a single assessment tool, and related method, that can assess the impact of various diseases on HRQOL. It is also desirable to have a system which scores everyone on a standard metric so that the results of various different diseases can be compared. Accordingly, there is a real and continued need in the art for improved systems and methods for the monitoring and assessment of impact of various diseases on HRQOL.

It is appreciated that these are but representative of certain needs in the art which various aspects of the present invention address and provide.

OBJECTS AND SUMMARY OF THE INVENTION

Therefore, it is an object of the present invention to provide an improved system that overcomes the shortcomings of the prior art. Accordingly, the present invention provides a system for remotely monitoring patients and for communicating the results of such monitoring to the patient and, optionally, to others.

It is an object of the invention to provide a new approach to standardizing disease-specific assessments of HRQOL to achieve the advantages of both generic questionnaires, which can be compared across diseases and treatments, and disease-specific questionnaires, which have greater sensitivity and specificity.

It is a further object of the invention to produce disease-specific impact scores, which will be comparable on a standard common metric across different diseases or age groups.

In accordance with an embodiment of the present invention, a system for assessing the impact of various ailments on a health related quality of life ("HQROL") domain of a patient comprises a testing module and an evaluation module. The HRQOL domain comprises a plurality of indicators of functional health and well being. The test module generates a customized test having a plurality of questions for the patient to determine the impact of the ailment on the HRQOL domain. Each question includes an indicator of functional health and well being as a result of the ailment. The indicator is stably scaled across ailments whose impact is to be assessed to establish a standardized common metric for comparing the impact of various ailments. The evaluation module evaluates, after each question, answers provided by the patient to estimate an ailment impact score and a confidence level in the accuracy of the estimated score. The evaluation module controls the test module to dynamically modify the test if the estimated confidence level is outside a pre-determined threshold.

In accordance with an embodiment of the present invention, the system for assessing the impact of various ailments on a HQROL domain of a patient as aforesaid, further comprises a standardization module for generating a standardized common metric of the impact of an ailment on the HRQOL domain across a plurality of ailments or age groups.

In accordance with an embodiment of the present invention, the standardization module of the system as aforesaid further comprises a uni-dimentionality, differential item functioning, item bank and ordering modules. The uni-dimensionality module performs a uni-dimensionality evaluation on a plurality of indicators of functional health and well-being impacted by the plurality of ailments to provide a first set of candidate indicators. The differential item functioning module performs a differential item functioning analyses on the plurality of indicators of functional health and well-being impacted by the plurality of ailments to provide a second set of candidate indicators. The item bank module builds an item bank of the plurality of indicators of functional health and well-being impacted by the plurality of ailments from the indicators that are members of both the first and second sets of candidate indicators to provide indicators that are stably scaled across the plurality of ailments or age groups. Lastly, the ordering module orders the indicators of functional health and well-being impacted by the plurality of ailments that are stably scaled across the plurality of ailments or age groups in accordance with the relative level of ailment impact defined by each to form a standardized common metric of the impact of an ailment on the HRQOL domain of the at least one patient across the plurality of ailments or age groups.

In accordance with an embodiment of the present invention, a method of assessing the impact of an ailment on an HRQOL domain of a patient comprises the steps of generating a customized test and evaluating answers to the customized test. The HRQOL domain comprises a plurality of indicators of functional health and well being. The customized test has a plurality of questions for the patient to determine the impact of the ailment on the HRQOL domain. Each question comprises an indicator of functional health and well being as a result of the ailment. The indicator is stably scaled across ailments whose impact is to be assessed to establish a standardized common metric for comparing the impact of various ailments. After each question, answers provided by the patient are evaluated to estimate an ailment impact score and a confidence level in the accuracy of the estimated score; and dynamically modifying the test if said estimated confidence level is outside a pre-determined threshold.

In accordance with an embodiment of the present invention, the method of assessing the impact of an ailment on an HRQOL domain of a patient as aforesaid, further comprises the step of generating a standardized common metric of the impact of an ailment on the HRQOL domain across a plurality of ailments or age groups.

In accordance with an embodiment of the present invention, the step of generating a standardized common metric of the impact of an ailment on the HRQOL domain across a plurality of ailments or age groups further comprises the steps of: performing a uni-dimensionality evaluation on a plurality of indicators of functional health and well-being impacted by the plurality of ailments to provide a first set of candidate indicators; performing a differential item functioning analyses on the plurality of indicators of functional health and well-being impacted by the plurality of ailments to provide a second set of candidate indicators; building an item bank of the plurality of indicators of functional health and well-being impacted by the plurality of ailments from the indicators that are members of both the first and second sets of candidate indicators to provide indicators that are stably scaled across the plurality of ailments or age groups; and ordering the indicators of functional health and well-being impacted by the plurality of ailments that are stably scaled across the plurality of ailments or age groups in accordance with the relative level of ailment impact defined by each to form a standardized common metric of the impact of an ailment on the HRQOL domain of the at least one patient across the plurality of ailments or age groups.

In accordance with an embodiment of the present invention, a computer readable medium comprises code for assessing the impact of an ailment on an HRQOL domain of a patient. The HRQOL domain comprises a plurality of indicators of functional health and well being. The code comprises instructions for: generating a customized test having a plurality of questions for the patient to determine the impact of the ailment on the HRQOL domain, wherein each question includes an indicator of functional health and well being as a result of the ailment, wherein the indicator is stably scaled across ailments whose impact is to be assessed to establish a standardized common metric for comparing the impact of various ailments; evaluating, after each question, answers provided by the patient to estimate an ailment impact score and a confidence level in the accuracy of the estimated score; and dynamically modifying the test if the estimated confidence level is outside a pre-determined threshold.

These and other objects and advantages will become more apparent after consideration of the ensuing description and the accompanying drawings.

BRIEF DESCRIPTION OF THE DRAWINGS

The following detailed description, given by way of example, and not intended to limit the present invention solely thereto, will be best understood in conjunction with the accompanying drawings in which:

FIG. 1 depicts a flowchart of a further aspect of the Assessment Method;

DETAILED DESCRIPTION OF THE EMBODIMENTS

Figure 2A:
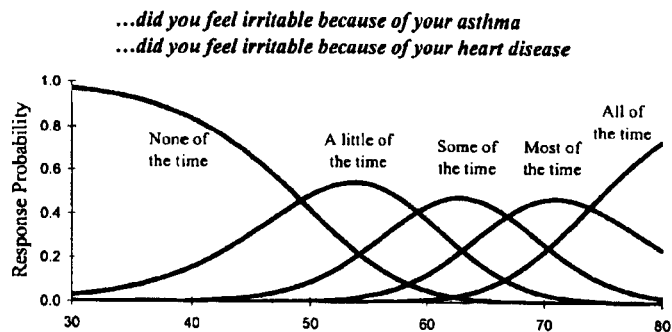
FIGS. 2A-2C depict a series of graphical representations of statistical assessment of two questions and responses thereto as provided by a group of respondents, as well as the graphical representations of a derived statistical assessment.

The definitions of the following terms as used in the specification are given by way of example to illustrate the concepts being discussed herein, and not intended to limit the terms solely to these definitions.

"Ailment"—A patient's condition which impacts on a health related quality of life domain of the patient. By way of non-limiting examples, these can include various diseases and conditions such as headache, hernia, rhinitis, asthma, overweight, osteoarthritis, diabetes, chronic obstructive pulmonary disease, depression, congestive heart failure, and rheumatoid arthritis, and the like.

"Assessment Method"—The monitoring system being described herein.

"Test Subject"—The person taking the test. Such person may be referred to as a "subject respondent", and when the test relates to health related subject matter, may be referred to as the "patient".

"Testlet"—One or more questions primarily directed to evaluating the status of a Test Subject relating to a domain.

"Test"—One or more testlets which are used to evaluate one or more domains.

"Domain"—An aspect or condition experienced or perceived by the test subject sought to be evaluated by a test or testlet. By way of non-limiting examples, these can include various health-related measures such as severity of headaches, level of depression, degree of personal mobility, self-perceived status, general well being, etc. Other non-health related aspects or conditions perceived by a test subject may also be considered as valid domains as "customer satisfaction", and the like. By way of non-limiting examples, these also can include a health related quality of life domain which can include: physical, social, role, emotional, and cognitive functioning, and the like.

"Test Session"—A single episode of the administration of a test. Frequently, a plurality of test sessions are used by the test subjects regarding the test subject with regard to that test subject's perception of their personal condition or perceptions thereof relating to one or more specific domains.

"Subject Group"—A set of one or more test subjects who are participating in the Assessment Method in order to evaluate one or more domains which are common to each of the test subjects making up the subject group. The subject group can be a single individual test subject, but usually comprise two or more test subjects. By way of example, the subject group may be one or more test subjects who are associated with each other due to a common domain sought to be evaluated. The evaluation may relate to the individual test subject as well as for the subject group. Examples of such may include a group of headache sufferers, one or more persons suffering depression, and the like. A still further example of a subject group may be one or more test subjects who are associated with each other due to a common variable, and the desire to evaluate the responses elicited from a particular test subject as well as the whole subject group related to the variable. By way of example, such a variable may be a pharmaceutical composition which is being administered to one or more of the test subjects making up the subject group. In another example, the variable may be the practice of a specific therapeutic procedure upon one or more of the test subjects comprised in the subject group. As a still further example, the subject group may be one or more test subjects receiving specific health related services from a common provider, such as specific doctor, or a group of doctors, or organization such as health maintenance organization (HMO), pharmaceutical company, etc.

"Survey Respondent"—A person participating in a survey used in the test generation process of the Assessment Method.

"Device"—An article, apparatus, or instrument capable of presenting information to a test subject relating to the Assessment Method, which is desirably also capable of receiving a reply from the test subject. By way of non-limiting example, exemplary test devices include stand-alone computers, one or more computers connected to a network, one or more computers connected to the Internet, a computer terminal or other device that may be provided in an information kiosk, Internet appliances, hand-held computers also frequently referred to as "portable digital assistants" (PDA), Web-TV devices, telephones (both wired and wireless), bi-directional wireless communication devices such as bi-directional pagers and the like, as well as paper forms. Ideally the devices are two-way communications devices, particularly devices which include a display means (such as a cathode ray tube, flat panel display, and the like) or other means for prompting an input (such as audio devices, speech synthesizers, and the like) and an input device (such as buttons, keyboards, computer mice, touch pads or touch screens and the like.)

The present invention comprises several processes or modules, including, but not limited to, test generation, testing or administering, evaluating and reporting. These processes of the present invention as well as others are described hereinafter.

In the test generation process or module, the system collects data from a pre-existing data pool or database of questions and answers, statistically assesses the data, and forms a test for subsequent use in the testing process and process (or administration and evaluation modules). In accordance with an embodiment of the present invention, the system collects data by generating a survey of questions with a list of possible answers and providing it to one or more survey respondents in order to elicit their responses thereto. The individual questions of the survey should be similar to, or, preferably, the same as the tests to be subsequently utilized in testing and evaluation. Such similarity, or identity, in questioning ensures a high degree of relevance and statistical accuracy between the initial results garnered from the survey and the subsequent operation of the Assessment Method. The test questions can be of any form, and essentially can be directed towards any of a wide variety of subjects. Preferably, however, the survey includes one or more questions related to each of one or more domains which are sought to be evaluated by the Assessment Method. In accordance with an embodiment of the present invention, the questions have a graduated scale of possible answers associated therewith. A question is associated with scaled responses that have at least two possible answers (such as "yes" or "no"), and, preferably, have a graduated scale of potential responses (such as integer numbers within a range "1, 2, 3, 4, 5", or "very bad, bad, fair, good, or very good"). The reasoning behind the preference for a larger number of possible answers is that a plurality of potential responses to any test question provides a response that is more precise than a simple "yes" or "no." Where one or more of the test questions, preferably a majority of the test questions, have graduated scales of potential responses associated therewith, the Assessment Method provides more accurate results.

The survey comprises one or more questions evaluating one or more of the domains that are perceptible to the survey respondents. The possibility of domains varies widely, and covers all subjects of interest in the Assessment Method. The scope of a domain varies from general areas of interest, such as general health as perceived by a subject respondent, to more specific areas of interest, such as personal mobility. In such an example, personal mobility or depression may comprise a more narrowly tailored subset of the broad general health domain. Hence, a broader domain can comprise subsets corresponding to domains of narrower scope.

The generation of the form and content of the individual questions on a survey may vary from survey to survey. However, known-art surveys provide good guidance in fashioning useful survey questions and the associated possible responses. Of course, these survey questions and their answers must be relevant to the domain sought to be evaluated.

It is appreciated that the survey can be administered according to the prior art procedures as long as the collected data is available for subsequent statistical assessments. Naturally, selection of the survey respondents plays a key role in ensuring the accuracy of the survey. Preferably, the survey respondents should closely correlate to the expected test subjects of the Assessment Method.

In an alternative to the data collection process or module as discussed herein, the actual generation and administration of a survey can be skipped when a data pool of existing survey test questions and answers, relevant to the domains sought to be evaluated in the Assessment Method, are already available. Accordingly, the pre-existing test questions and answers can be utilized directly. However, the pre-existing survey questions and answers should be used only when they are relevant to the domains at issue.

In accordance with another embodiment of the present invention, the system establishes threshold limits, the minimum statistical probability which are considered to be acceptable for the valuation of the condition of a test respondent with respect to a particular score level and/or a particular domain. These limits can be arbitrary or based on a body of data, such as the survey questions and responses. Preferably, the threshold limit values determine the number of questions from a Testlet to be provided to a test respondent. For example, where the limiting value for a particular Testlet is relatively low, i.e., 50% probability, then it may be sufficient to query the test subject with a relatively small number of questions from that Testlet. Based upon the responses received from the test subject to each of the questions in the Testlet, the present system compares these responses against the statistical assessments previously generated in order to determine the cumulative probability of the status of the test respondent with regard to the condition being evaluated in the domain. When such a cumulative probability meets or exceeds the threshold limits, the testing from the Testlet is concluded. This process or module provides a means for optimizing or limiting the number of questions which in turn also reduce the burden imposed on the test subject. Conversely, where a high degree of statistical accuracy is desired with regard to analyzing the status of a test subject with respect to a particular domain, then the present system may need to use a larger number of questions from the Testlet during the test.

In accordance with a further embodiment of the present invention, the system includes the testing and processes for administration or evaluation modules. The questions of the test, which have been assembled in the test generation process or module, are presented to one or more test respondents on a device. Examples of such devices have been briefly mentioned above, and will be discussed in more detail herein. The device must be capable of presenting these questions in a discernible form as well as receiving the response to the particular question being elicited from the test subject. Subsequent to the receipt of such a response, the system compares the response against the statistically assessed responses to the same test question, which had been presented in the survey and/or presented to the test subject in one or more prior tests. The comparison includes an evaluation of the statistical probability of the appropriate assessment of the test subject within the domain being evaluated. If this statistical probability equates to or exceeds the threshold limits which have been previously assigned, then the Testlet is concluded. Alternately, if this threshold value is not attained, then the present system presents another question from the Testlet to the test subject. Again, the present system compares the response against the statistical assessment of the same (or similar) question from the test survey and/or a prior test. Thereafter, the system performs a statistical assessment based on the current responses to the test questions from the Testlet in order to determine the statistical probability associated with the combination of answers to the Testlet questions received thus far. This analysis may include the determination of the likelihood of the responses to each question for persons at a specific scaled value within the domain, as well as the statistical probability of combination of responses to these questions. Preferably, such statistical analysis of the combination of questions also includes the likelihood of consistent responses, as well as the likelihood of erroneous responses. Based on the results from such statistical analysis, the present system tests the probabilities against the threshold limit again, and if the value equates to or exceeds such a threshold limit, the Testlet is concluded. Otherwise the process repeats itself until the Testlet concludes.

In an embodiment of the testing process or module of the present invention, the system can establish an increased level of accuracy as well as inquiry towards one or more domains from a larger set of domains. For example, the system can establish a higher threshold limit to the domain of particular interest and/or diminish the threshold limit to the domains of lesser interest. In this way, the system streamlines the process by not requiring an unnecessary amount of additional questions for domains of reduced interest, while requiring a increased number of questions for a domain of particular interest. Such a process reduces the burden on the test subject without reducing the statistical accuracy of the Testlet.

In an embodiment of the present invention, the reporting process or module comprises the scoring and presentation of responses elicited during the testing process. According to one alternative, the system immediately presents the test subject with the results of one or more of the Testlets upon the conclusion of such Testlet. In another alternative, the system withholds the results until the conclusion of the test. The system can present these results in a simple form, such as a simple numerical readout, or in a graphical format such as curves, slopes, graphs, and the like. Preferably, the system presents the results in context. For example, it will present the scored Testlet results with a comparison to the average responses from one or more other test subjects who have taken the same Testlet. Such comparisons are most relevant when the test subject belongs to a group. As a further alternative, the system presents the results in comparison with historical results. Such historical results include, but are not limited to, the results from prior test sessions for the same Testlet by the same subject, the results of Testlets from the test having just been administered as compared to the cumulative results and historical variations of a group of test subjects, the results of the Testlets having just been administered as compared to both the results from prior art test sessions for the test subject, as well as the cumulative scores of a group of test subjects over the same time interval. In this manner, the system can present the test subject with relative changes or progress over a timed interval, such as a period of days, weeks, months, years, etc. The time intervals can vary and are not critical to the Assessment Method. Where, however, a regularly-timed interval is preferred, then it is also preferred that the test sessions occur approximately at the same corresponding timed intervals, i.e., monthly, weekly, daily, etc. In such a manner, uniform time intervals can be conveniently established. Such also facilitates monitoring of a test subject.

A particular advantage of the Assessment Method as described herein is in that unlike many prior art surveys which are inflexible and static, the test method of the present invention is dynamic. What is to be understood by static is that a survey is repeated for each test session and there is no possibility of altering the number of questions relating to a domain, or their sequence, or indeed the length of the survey. As has been noted above, such is particularly burdensome upon individuals, particularly where such individuals need to have the tests administered several times, such as in regular periodic intervals. Burdensome surveys are known to be more prone to errors, including misunderstanding and/or misanswered questions, as well as questions for which no responses have been provided. According to an aspect of the Assessment Method, during the administration of a test, based on the responses to questions elicited, the Assessment Method is capable of increasing or decreasing the number of questions presented to the test subject. As has been noted above, wherein a threshold limit has been established for a particular Testlet, then the Assessment Method need not present questions which exceed the minimum number of questions required in order to satisfy the threshold limit. The converse is also true, as wherein there may be a domain which is of particular interest or concern with respect to the test subject, then the threshold limits may be established at an increased level such that a larger number of questions from a Testlet need be presented prior to the conclusion of the Testlet directed towards assessing the status of the test subject with regard to their condition respective to a domain.

In accordance with an embodiment of the present invention, the Assessment Method establishes the test for one or more domains based on an increased level of accuracy as well as inquiry towards one or more domains from a larger set of domains. This can be done, for example, by establishing a higher threshold limit to the domain of particular interest and/or diminishing the threshold limit to the domains which are of lesser interest. The overall benefit of this is that wherein a test is directed towards evaluating several domains relevant to the test subject, then additional questions are not required for domains which are of reduced interest, while increased number of questions related to a domain of particular interest can be provided during the test. Such reduces the burden on the test subject without reducing the statistical accuracy of the Testlet.

A further embodiment of the evaluation or reporting process or module of the present invention comprises the provision for a method of estimating "skipped" answers to test questions. For example, when a test subject omits the response to one or more questions, then, based on the statistical analysis of the questions which have been properly responded to, the system calculates an estimate of the likelihood of the subject's response to the "skipped" question. More specifically, for a Testlet having a plurality of questions, i.e., five questions, directed towards evaluating a specific domain, but only four of the five questions have been responded to, a statistical analysis determines the correspondence between the four properly responded to questions and the fifth omitted question. If there is a sufficient level of consistency between these answers, namely a satisfactory degree of statistical probability that the answers to each of the four questions responded to correspond to a specific value, or limited range of values represented by the ordinate axis, then the system can provide a reasonable prediction that the skipped question would have been responded to with the available response which corresponds to that same ordinate axis value, or ordinate axis value range.

Further embodiments of the process or evaluation module of the present invention include the ability to utilize the results from the survey and particularly from the test administered and the resultant scales representative of their condition with different scales taken from different tests. The system utilizes various psychometric evaluations and scales to indicate the status of test subjects within certain domains. Prior art system have not been able to accurately interrelate and provide a correlation between the scales of these different psychometric evaluation techniques. In this embodiment of the present invention, the system uses the results of the Assessment Method with different scales and correlates between the scales utilized by different first psychometric analysis techniques. For example, the system presents a subject respondent with a plurality of questions in each Testlet. The system scores the responses to questions relative to the scales of both the first and second psychometric techniques. The system can establish a survey for each of the techniques and score the results on both scales simultaneously. At the conclusion of the test, and especially at the conclusion of a plurality of test sessions, the system can establish a correlation between these varying scales based on a derivation from the statistical analyses of consistent responses with respect to a subject's perceived condition relative to a domain. This is an invaluable aid in advancing psychometric analysis.

In an embodiment of the present invention, the system provides a further advantage by allowing the patient to self-administer a test. In another embodiment of the present invention, the system provides yet a further advantage through subject assessments of survey results. The system allows the subjects of the test to assign subjective measures to their responses based upon the individual subjective assessment and evaluation of their condition with regard to a domain and the scale of that domain. The system accounts for variations in this subjective assignment of values according to the domain, particularly when the initial survey questions and answers are statistically assessed and optionally, but in many cases, normalized against the overall population of the test subjects participating in the survey.

An advantage of the Assessment Method of the present invention relates to the type of reporting information which is provided to the test subject. As stated herein, many prior art surveys provide information which is of an objective nature, as these are frequently based on the objective observations of individuals observing the test subject. These are not necessarily based upon questions and responses elicited directly from the test subject without the intervention of such an observer. In contrast, the Assessment Method is based upon the subjective measurements which are assigned by the test subjects themselves who participate in the Assessment Method. These are believed to be particularly accurate as they are not based upon an external, imposed scale of a condition regarding a particular domain being evaluated, but are based upon the individual subjective assessment and evaluation of their condition with regard to a domain based on the scale of the domain. Variation in this subjective assignment of values according to a domain are accounted for in the Assessment Method, particularly when the initial survey questions and answers are statistically assessed and optionally, but in many cases, normalized against the overall population of the test subjects participating in the survey.

A still further important feature of the Assessment Method lies in the presentation of the Testlet scoring results. As has been discussed above, the data collected from test subjects is based on subjective data, i.e., their own perceptions and not based upon the perceptions of others viewing a test subject. According to particularly preferred embodiments, the information provided in the output of a report is presented in a fashion which is particularly meaningful to the test subject. This includes the forms and reports noted herein, such as those providing a historical assessment of the progress of a test subject with regard to one or more domains; a historical progress of the test subject with regard to one or more domains as against the historical progress of the subject group; and test score results from a particular test as compared to the test score results of prior test subjects having participated in the Assessment Method, being those participating in the survey, those participating in prior test sessions, or any combination of both of these groups. It is also foreseen that the content of information and/or format of the report can be established by the test subject, or by other individuals who may be participants or healthcare provider. It is appreciated that such modification permits for a wide degree of modification and contemplates the generation of customizable reports, and the ability to modify the report at any time by the test subject or other individuals. This provides a degree of flexibility to individuals who may be participating or monitoring the tests.

The Assessment Method described herein can be used over a broad range of subject matter.

Personal health monitoring is an area which is particularly advantageously practiced utilizing the Assessment Method described herein. Personal health monitoring can be used by test subjects to evaluate their own perceived condition relating to one or more domains relating to various aspects related to physical and/or emotional health. By way of non-limiting example, such domains include the impact of headaches, physical fitness, emotional fitness, depression, the impacts of asthma, as well as others not particularly elucidated here. One or more of these domains may be evaluated by the administration of Testlets having questions corresponding to each or one or more of the domains, or in the alternative, only a single domain, and a corresponding Testlet can be administered. While the test can be administered once, thereby the test subject can obtain a general measure of their responses relative to a larger population (such as of survey respondents and/or other test subjects), in an advantageous variation, the Assessment Method collects and stores the results of individual test sessions for the test subject. The test subject, upon repeating the test, may, over a period of time, perform several test sessions which can be used to assess the changes in the perceived status of the test subject with regard to these domains. As is noted above, this information can be graphically provided to the test subject. Further, it is contemplated that this information related to a test subject is maintained by the Assessment Method in a "health notebook". Such a health notebook is a visual representation of the collection of data relating to the test subject's responses to test questions which have been obtained, and analyzed during one or more test sessions. Such a health notebook is conveniently readily accessible from a device, and the results of the contents of the health notebook are readily printable for review and storage by the test subject apart from the device.

In accordance with an embodiment of the present invention, the Assessment Method or system assess the health status of a patient by providing a customized test that dynamically changes based on the patient's responses to the questions. The test module or process initially estimates a score, e.g., 50%, and generates a customized test having a number of questions relating to a health domain to be assessed. The health domain relates to a condition experienced or perceived by the patient, including but not limited to, severity of headaches, level of depression, degree of personal mobility, self-perceived status, effectiveness of a treatment, and general overall health. In accordance with an aspect of the present invention, the Assessment Method and system can be also utilized to assess non-health related conditions, such as, job satisfaction, opinion polling, personality test, customer satisfaction, human relationship, and the like. The administration module or process presents one question at a time to the patient. After each question, preferably after the patient's response to the question, the evaluation module or process calculates or re-estimates the score and a confidence level in the accuracy of the estimated score. The evaluation module or process estimates the score based on the various statistical analyses of the responses received from test subjects or other patients. Depending on the health domain, the evaluation module sets a pre-determined threshold based on the patient's estimated score. The evaluation module or process dynamically modifies the test until the estimated confidence level is within the pre-determined threshold. That is, if the evaluation module or process determines that it can estimate the patient's answers to the questions in the test, it terminates the test since it has enough information to assess the patient's health status. This advantageously reduces the burden on the patient, since an assessment can be made without the patient answering all of the questions of the test or survey.

If the estimated confidence level is outside the pre-determined threshold, the evaluation module ranks the questions based on the estimated score and selects one of the questions that has not been administered or provided to the patient. Preferably, the evaluation module selects the question with the highest rank that has not been previously administered to the patient.

A further aspect of the present invention relates to an apparatus for performing the Assessment Method. This apparatus may be specially constructed for the operation of the Assessment Method, or it may comprise a general purpose computer as selectively activated or reconfigured by a computer program stored in the computer. Various general purpose machines may be used with programs written in accordance with the teachings herein. It is also possible that it may in certain instances be advantageous to construct more specialized apparatus to perform the required steps of the Assessment Method. Non-limiting examples of such machines include the devices described previously, as well as further machines and systems of machines described hereinafter. These non-limiting examples include stand alone computer, or connected to a two or more computers on a computer network, such as a local area network (LAN) as well as larger networks such as the Internet.

In one aspect of the present invention there is provided an assessment and monitoring system which comprises a host computer facility supporting wired or wireless network delivery of user-relevant components, such as tests, and output such as reports of the Assessment Method to multiple remote user interface devices.

In another aspect of the invention there is provided an assessment and monitoring system which comprises a programmed general purpose computer which is programmed to operate the Assessment Method.

In another aspect of the invention there is provided an assessment and monitoring system which comprises computer-readable media which contains the instructions for use by a programmable general purpose computer necessary to operate the Assessment Method.

In another aspect of the invention there is provided an assessment and monitoring system which comprises one or more devices which are connected to a host computer facility which is programmed to operate the Assessment Method. The devices include without limitation computer terminals, general computers connected to the host computer facility, wireless devices including wireless telephones, two-way communications devices, or other devices which include an display means (such as a cathode ray tube, flat panel display, and the like) or other means for prompting for an input (such as audio devices, speech synthesizers, and the like) and an input device (such as buttons, keyboards, computer mice, touch pads or touch screens and the like.)

The Assessment Method according to the invention is conveniently adapted for implementation on physically compact, portable, user-interface devices such as small portable personal computers, and particularly hand held devices known as personal digital assistants. Those skilled in the art will understand that the system can readily be used on or adapted to other hardware platforms, for example, a desktop computer and can be expressed in different software interfaces from that shown in this specification, especially ones that use different input devices such as keyboards, touch pads or touch screens and the like.

The Assessment Method can be implemented in software, and can be provided for use for single-user operation on a stand-alone personal computer, or for multi-user operation on a network for use by a number of test subjects. Particularly useful are embodiments wherein a test subject is remotely administered a test session on a device, and the device is in communication with a host computer via a bi-directional wired or wireless connection. Examples of the former may include local area networks (LAN), wide area networks (WAN) as well as the Internet. Examples of the latter include connections wherein wireless means such as transmission via IR signals, microwave or radio-frequency communications are employed for at least part of the communications path between a device and the host computer. Thus a preferred embodiment of the invention comprises a host computer facility supporting wired or wireless network delivery of the tests and test sessions, as well as related information such as reports and the like, to multiple remote user interface devices. Such an embodiment is further preferred as a host computer facility can be conveniently used for the administration of tests in test sessions, statistical assessment of information regarding tests and test sessions, as well as related functions. One such function is operating as a central repository for maintaining records relating to test sessions, the identity of test subjects and subject groups. A further such function is operating as a central administration center wherein changes or modification to the content of the Assessment Method, particularly changes to the questions and format of the test and Testlets can be made.

The host computer facility provides data, or access to data, data processing and communications resources for test subjects operating the devices. The host computer facility can be a server or cluster of servers with associated data storage volumes, and at least one intelligent client providing access to the server or servers. The host computer facility can call upon a variety of external resources and functions as a marshalling and processing center for organizing resources for utilization by limited capacity devices. In a preferred embodiment it is a co-ordination point on a network for a device used in the administration of the Assessment Method. Optionally, the network accesses or includes a number of remote database sources providing access to elements both within and without the host computer facility.

The format of the test, test questions and reports may vary widely but desirably are arranged to provide a readily understandable presentation of information on the device upon which the test is administered. Desirably such a format for such information is provided on screens in a user-friendly format, and provides a user-friendly interface for presenting information and for providing a response to questions. Elements of such user-friendly interfaces are familiar to many computer users, such as activatable buttons, pointers, scroll bars, icons, arrow key, drop-down menus, windows and other screen symbols designed for actuation by a pointing device, for example, a mouse or trackball. More preferably, for embodiments implemented on a handholdabe computer, the pointing device is a pen or stylus. The Assessment Method itself can be programmed for operation in any suitable computer language (i.e., Pascal, C/C+/C++, assembly language, BASIC, etc.) and on any suitable operating system (i.e., UNIX, LINUX, Microsoft WINDOWS, Macintosh OS, etc.).

A further example of devices which find use with the instant invention are small handholdabe computers (sometimes referred to as "personal digital assistants" as well as "PDA"s). An example is the Pilot®V handheld computer vended by Palm Inc. and the Visor® handheld computers vended by Handspring Inc., as well as the Hewlett-Packard Jornada® handheld computers. These handheld computers include a central processor unit, programmable memory, a display/input means, and a means for communicating with a computer or computer network. These latter means include a "wired" connection to a computer or computer network, as well as "wireless" communications capabilities such as radio wave or infrared wireless communications means enabling them to exchange data with a computer or computer network without the cost or inconvenience of hard wiring.

Pursuant to certain user-adaptive aspects of this invention, the screens are readily adapted to the test subject. This adaptive characteristic is a valuable benefit as the small and portable nature of the PDAs introduce great convenience in the administration of a test session, and the simplicity of interacting with such devices and providing responses to questions presented on the screens facilitate compliance with a periodic schedule of test sessions. The ease of use and suitability of the Assessment Method to such keyless or minimally keyed platforms, especially PDA's, is promoted by minimizing the need for actual text or data entry by the user and by emphasizing instead data selection by selection from among possible responses to questions. Preferred embodiments of the invention allow quick pen selection of data items through columnar "pick lists" of possible responses.

A further example of an interactive interface and delivery system suitable for use as a device for administration of the Assessment Method is a wireless telephone. A wireless telephone is suitable for use as a device as it provides bi-directional communication capabilities with a host computer or other computer, a keyboard or microphone suited for providing an input indicating selection of a response to a question, and a screen or speaker which can be used to provide questions to a test respondent in an audially and/or visually perceptible manner. Wireless telephones are also compact and portable and offer conveniences and benefits similar to PDA's discussed above.

A further example of an interactive interface and delivery system suitable for use as a device for administration of the Assessment Method may be an 'information kiosk'.

Such an information kiosk includes a touch-sensitive display, keyboard or other input means so that the test subject may respond to questions provided during the test. In other operational respects such an information kiosk is similar to a conventional computer working independently of a network, or similar to a computer terminal or computer attached to a network but is available in public spaces and are intended for public access. Such might be also viewed as a 'public computer' or 'public computer terminal.' The benefits of such an information kiosk is that the test respondent need not be provided with a device in order to participate in the Assessment Method, but may participate from an information kiosk. Such lowers the overall costs which might otherwise be associated with the necessity of providing devices to test subjects, particularly where a larger number of test subject comprise a subject group. Further the public availability of such information kiosks may ensure better compliance with any regimen for which the Assessment Method may be utilized.

The present invention also comprises an approach to assessment of disease impact that combines the advantages of generic and disease-specific questionnaires. This approach builds on a conceptual framework for the relation between clinical parameters, specific symptoms, and disease impact and on a statistical model for the combined effect of question type and disease condition. Specifically, this approach builds on: (1) an item bank representing the most frequently measured domains of disease impact (e.g., role functioning, social functioning, physical functioning, and psychological distress), standardized across diseases, and (2) instructions to assess the impact of a specific disease (e.g., arthritis, diabetes) in answering each questionnaire item.

This model extends the psychometric Item Response Theory (IRT) models, which have been used in educational testing (Thissen D & Wainer H (2001). *Test Scoring*. Mahwah: Lawrence Earlbaum Ass, which is incorporated herein by reference in its entirety) and in health outcomes research (Ware J E, Jr. (2002). Conceptualization and Measurement of Health-Related Quality of Life: Comments on an Evolving Field. *Arch Phys Med Rehabil*, 83 (*Suppl* 2), S1-S9, which is incorporated herein by reference in its entirety). The IRT model and computerized adaptive testing (CAT) are used to deliver a dynamic assessment of disease impact that has far more precision for a given test length than a traditional questionnaire. This method allows a unified approach to the disease-specific assessment of disease impact and comparison of impact across diseases. This method also uses IRT and CAT software to yield more practical and precise assessments over a wide range of disease conditions and severity levels—eliminating "ceiling" and "floor" effects.

In accordance with an embodiment of the invention, CAT software can be programmed to select and administer the most informative and relevant disease impact questions for each patient, with consideration of the clinical application. Standardization of the content of disease-specific impact items and calibration of these items across diseases makes it possible to achieve more responsive outcomes measures, while enabling meaningful comparisons across diseases/treatments. Previous work has used IRT methodology to develop a bank of items with equivalent item calibrations across five diseases. The aims of the present invention are to analyze existing data sets to evaluate the equivalence of these item calibrations across age groups and to test the feasibility of the Disease Impact CAT approach for elderly patients in a clinical setting. In accordance with an embodiment of the invention a Disease Impact CAT can be used to collect data from 100 middle aged and elderly patients within five groups: arthritis, depression, chronic obstructive pulmonary disease, diabetes, and osteoporosis. Separate feedback reports can be developed for the patients and the clinicians. Feasibility can be evaluated in terms of respondent burden, range of levels measured, item usage, and response consistency, as well as the clinicians' and patients' experience using the CAT tool of the present invention and the feedback reports. In accordance with an embodiment of the invention, the product of the invention can be a Disease Impact CAT with evidence regarding feasibility and acceptance. In accordance with an embodiment of the invention, a comprehensive Disease Impact CAT Assessment System, standardized across primary and comorbid chronic diseases/conditions, in terms of psychometric performance and usefulness in clinical research and practice can be developed.

A psychometric evaluation of the viability of the present approach was performed among adults in six disease groups: headache, asthma, rhinitis, osteoarthritis, rheumatoid arthritis, and congestive heart failure (see e.g., Bjorner J B, Kosinski M, & Ware J E, Jr. (2003a). Calibration of an item pool for assessing the burden of headaches: an application of item response theory to the headache impact test (HIT). *Qual Life Res*, 12, 913-933; and Kosinski, M., Bjorner, J. B., Ware, J. E., Jr., Strauss, W., & Sullivan, E. Applications of Computerized Adaptive Testing to the Assessment of Osteoarthritis Impact (submitted). *J Clin.Epidemiol*, (in press), which are incorporated herein by reference in their entirety). One of the purposes of the present invention is to evaluate the generalizability across age groups of an embodiment of the present invention's approach to disease impact assessment and the feasibility of applying the present invention's approach in clinical practice by:

a. Analyzing existing data sets to evaluate the equivalence of item calibrations across age groups and to develop clinical benchmarks for interpretation of disease impact scores;
b. Developing a CAT of disease impact;
c. Developing feedback reports for the patient and for the clinician. The reports can contain guidelines for interpreting patient scores;
d. Testing the feasibility of the CAT among middle aged and elderly patients with five specific conditions: Osteoarthritis, Depression, Chronic Obstructive Pulmonary Disease, Diabetes, and Osteoporosis. The evaluation can be based on:
  1) Respondent burden, range of levels measured, floor and ceiling effects, and item usage;
  2) A psychometric evaluation of whether each patient's pattern of responses is consistent with the hypothesized IRT model;
  3) The patients' evaluation of the assessment situation and the usefulness of the patient feedback report;
  4) The clinicians' evaluation of the usefulness of the clinician feedback report.

The present invention uses available data to evaluate whether the disease impact approach disclosed herein is psychometrically generalizable across age groups (i.e., whether the item calibrations are stable over age). Data (n=100) can also be collected to assess the feasibility of the approach of an embodiment of the present invention among elderly compared to middle aged patients in a primary care setting.

An embodiment of the present invention can be a comprehensive disease impact CAT, with preliminary evidence regarding feasibility, acceptability and empirical performance. In accordance with an embodiment of the invention the comprehensive disease impact CAT can be a fully functional CAT including a plurality of diseases for which impact can be assessed.

Figure 6:
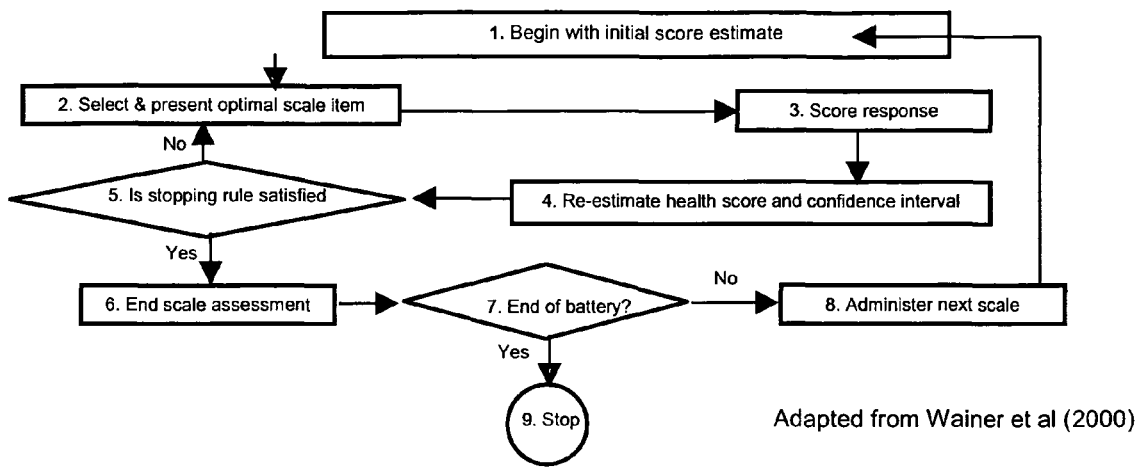
FIG. 6 depicts a flowchart of a further aspect of the Assessment Method.

The basic notion of an adaptive test is to mimic what an experienced clinician would do while assessing a patient. A clinician learns most when he/she directs questions at the individual's approximate level of health and functioning. Administering items that are either too easy or too hard provides little information. CAT employs a simple form of artificial intelligence that selects questions tailored to the test-taker, shortens or lengthens the test to achieve the desired precision, scores everyone on a standard metric so that results can be compared, and displays results instantly (Wainer H, Dorans N J, Eignor D, Flaugher R, Green B F, Mislevy R J et al. (2000). *Computerized Adaptive Testing: A primer*. (2 ed.) Mahwah, N J: Lawrence Erlbaum Associates, which is incorporated herein by reference in its entirety). Each test administration is adapted to the unique level of impact for each respondent. For example, an adult who is able to "walk 50 feet" is not asked to respond to a question about "walking 10 feet." In practice, this approach minimizes the number of items that are administered to an individual to obtain an estimate of the level of disease impact he/she experiences. The adaptive software of an embodiment of the present invention first asks a question in the middle of the range of impact, and then directs questions to an appropriate level based on the individual's responses without asking unnecessary questions. On the basis of the response to the first item, a score and confidence interval are estimated, then the next optimal item is presented and a response is recorded (see FIG. 6, which illustrates the logic of computerized adaptive testing of an embodiment of the present invention). With administration of the next item, the score is re-estimated along with a unique confidence interval. The computer algorithm determines whether the stopping rule has been satisfied. If satisfied, the assessment of that concept ends. If not satisfied, new items are administered in an iterative fashion until the stopping rule is satisfied. By altering the stopping rule, it becomes possible to match the level of score precision to the specific purpose of measurement for each individual. For example, more precision in scoring can be needed to monitor individual progress than to identify presence of disease impact for an individual respondent.

The psychometric methods of an embodiment of the present invention that make it possible to calibrate questionnaire items on a standard metric ("ruler") also yield the algorithms necessary to run the "engine" that powers CAT assessments. These statistical models tell us how likely a person at each level of function is to be described with each response to each survey question. This logic is reversed to estimate the probability of each impact score from a particular pattern of item responses. The resulting likelihood function makes it possible to estimate each person's score, along with a person-specific confidence interval. In principle, an unbiased estimate of disease impact (i.e., an estimate without systematic error) from any subset of items that fits the model is attained. The number of items administered can be increased to achieve the desired level of precision. Features of the software of an embodiment of the present invention that make it particularly suitable for the research include options for setting stopping rules on the basis of: (a) the accuracy of the score estimate (e.g., confidence interval<preset value), (b) maximum number of items (e.g., five or fewer), (c) a set number of items (e.g., most accurate estimate possible with 5 items), or (d) in terms of whether the probability of being above or below a pre-set score cut-off meets a particular criterion value (e.g., positive screen for substantial disease impact). Further, the criterion for each of these stopping rules can be set to vary according to score level. The likelihood function can also be used for purposes of monitoring the quality of data for each respondent and for estimating scores even if some responses are missing.

The market for a disease impact assessment system of the present invention that is comprehensive and precise and practical is substantial. Current disease-specific assessment tools are typically directed at the severe end of the disease spectrum and do not permit comparison of impact across diseases. Better tools are needed for clinical research evaluating new treatment options. To meet the needs of disease management, the challenge is even greater. Assessment tools that meet clinical standards of precision at the individual patient level are required. Current tools rarely meet these standards. By developing a large bank of items on disease impact and calibrating them on a common metric, an embodiment of the present invention is able to provide a precise assessment of disease impact. A traditional static survey using this item bank would, for many patients, require a half-hour to complete. Fortunately, this breakthrough in measurement can be the basis of a very efficient and successful commercial product using computerized adaptive testing (CAT) software of an embodiment of the present invention. The result is very brief assessments that meet clinical standards of precision over a very wide range of scores, while substantially reducing respondent burden and data collection costs. The viability of this concept has been proven for assessment of headache impact using the software of an embodiment of the present invention. During a free public offering of CAT assessments of headache impact using the software of an embodiment of the present invention and the initial HIT item pool, the number of "hits" on www.amIhealthy.com increased from 2,000 per day to more than 1.2 million per day with no increase in costs.

Among the many lessons from that experience and follow-up studies of patients and caregivers (Ware J E, Jr., Kosinski M, Bjorner J B, Bayliss M S, Batenhorst A, Dahlof C G et al. (2003). Applications of computerized adaptive testing (CAT) to the assessment of headache impact. *Qual Life Res,* 12, 935-952; and Bayliss M S, Dewey J E, Dunlap I, Batenhorst A S, Cady R, Diamond M L et al. (2003). A study of the feasibility of Internet administration of a computerized health survey: the headache impact test (HIT). *Qual.Life Res,* 12, 953-961, which are incorporated herein by reference in their entirety), the importance of a very user-friendly front end that allows for true integration with clinical practice or disease management services and very short and user-friendly patient and caregiver reports including simple interpretation guidelines was shown. Simple improvements made to the first page reduced "dropout" rates more than 50%. It is not enough to offer the best possible disease impact measurement. Thus, customized front end presentations and very efficient feedback reports are a crucial part of the software and services package of an embodiment of the present invention for monitoring disease impact.

Standardization, which can lead to the widespread adoption of concepts and measures, is another key element of an embodiment of the present invention. The development and inner-workings of the present invention's standards are documented thoroughly in user's manuals and report summaries in the peer-reviewed literature. The policies of the present invention provide for royalty-free access to the tools of the present invention for academic/scholarly research (leading to more than 4,000 SF-36 publications to date) and require that commercial users pay a royalty which is used to support research and development, and also provides a return on investments. A comprehensive and efficient disease impact assessment system of an embodiment of the present invention with established guidelines for its use in patient screening and interpretation guidelines for use in outcomes monitoring can be very successful in the health care marketplace.

Another key aspect of the strategy of an embodiment of the present invention is the expansion and evaluation of the Disease Impact CAT of the present invention for a number of additional diseases. This evaluation can partly be based on CAT only and partly be based on fielding the total item bank with new disease conditions to further evaluate the stability of item scaling across diseases. The advances in connectivity provide efficient, effective means for administering such tools in office-practice settings, in patients' homes and in numerous other settings.

The societal benefit that comes from improving the treatment of disabling conditions is unequivocal. The commercial opportunities that exist are also quite clear and quite broad. Potential purchasers of the assessment system of an embodiment of the present invention include provider groups, insurers, disease management companies and employers. A significant advantage of the present invention is that the assessment tools can be provided to such clients at a very small administration fee per individual. The CAT system of an embodiment of the present invention can be delivered through the Internet, as a stand-alone application on laptop or desktop computers, or as a computer-assisted interview.

An embodiment of the present invention combines the advantages of generic questionnaires (e.g., the SF-36), which can be compared across diseases and treatments, and the greater sensitivity and specificity of disease-specific questionnaires. By greatly lowering data collection costs, reducing respondent burden, eliminating "ceiling" and "floor" effects and increasing the precision of individual patient scores, routine monitoring of HRQOL can become feasible as a clinical tool. Making repeated and individualized patient reports available to patients and to caregivers in real time can radically improve both the processes of care and the very understanding of the nature of disease impact.

An embodiment of the present invention uses CAT to achieve a breakthrough in the information readily available for improving quality of care and research on chronic diseases. It can do so by informing history-taking with psychometric science, adding rigor to patient assessment at the clinics and offices where patients receive their care and, via the Internet, in patients' homes. These techniques can improve the precision with which nurses, social workers, physicians and other staff record patients' functioning and well-being, allowing for better care and clinical research, and the information can be integrated into a complete electronic medical record, promoting comprehensive patient care.

The concept of disease impact presented herein has important connections to the concept of participation, proposed by the WHO and defined as "involvement in a life situation" (World Health Organization (2001). *ICF: International Classification of Functioning, Disability, and Health.* Geneva: WHO, which is incorporated herein by reference in its entirety). Previous attempts to measure this social dimension of health as a generic term did encounter problems, since operationalization of "social well-being" (World Health Organization (1948). World Health Organization constitution. In *Basic Documents* (Geneva: WHO, which is incorporated herein by reference in its entirety) was affected by many non-health factors and not strongly associated with the person's own global health assessments (Ware, Jr., 1995). However, the assessment of the impact of a specific disease of an embodiment of the present invention on a range of "life situations" seems to overcome these problems.

The analyses presented herein are also important because they can specifically address the question of comparability of results across age groups and the applicability of the CAT approach among the elderly. Psychometric tests of an embodiment of the present invention can be used to assess whether the concept of impact is stable across age groups. Since concepts like impact and participation (see above) involve social and role functions, it is possible that the meaning of impact changes with age. Modem psychometrics discussed herein provide strong tools for the evaluation of such effects and, if found, the ability to correct for these changes to ensure comparable measurement across age groups (see, e.g., Bjorner J B & Kristensen T S (1999). Multi-item scales for measuring global self-rated health. Investigation of construct validity using structural equations models. *Research on Aging*, 21, 417-439, which is incorporated herein by reference in its entirety). Testing can be used to evaluate whether a CAT approach is acceptable to elderly patients and how a CAT can be designed to maximize acceptability. In recent strategy documents from the NIH, the use of CAT has been promoted as a technique that potentially could revolutionize how symptoms and treatment outcomes are assessed (NIH (2003). *Re-Engineering the Clinical Research Enterprise*. Bethesda, Md.: NIH, which is incorporated herein by reference in its entirety). Thus, CAT can take a prominent place in the assessment of HRQOL. It is therefore important to assess how an elderly population that has limited experience with computers can react to computerized assessments and how these can be designed to be most acceptable to elderly patients.

Figure 4:
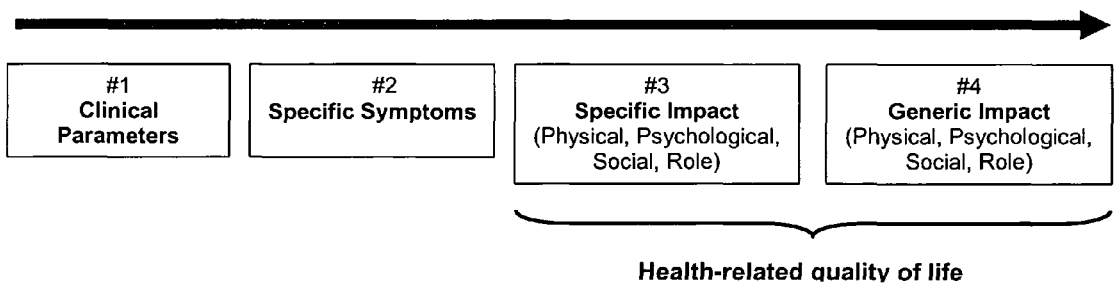
FIG. 4 depicts a continuum flowchart of a further aspect of the Assessment Method.

In accordance with an embodiment of the present invention, a conceptual framework for constructing disease-specific and generic HRQOL measures for clinical outcomes research makes important distinctions between domains of health and their operational definitions. (see FIG. 4). FIG. 4 portrays a specific-generic continuum (Ware, Jr., 1995; Wilson I B & Cleary P D (1995). Linking clinical variables with health-related quality of life. A conceptual model of patient outcomes. *JAMA*, 273, 59-65, which is incorporated herein by reference in its entirety), rather than a simple categorization of specific and generic concepts and measures. For example, as one moves from the left to the right of FIG. 4, the measures change from being the most highly specific and objective clinical measures (box 1), to disease-specific symptoms (box 2), to specific measures of disease impact (box 3), and to generic measures that are applicable across chronic disease and treatment groups. Measures in boxes 3 & 4 of FIG. 4 attempt to capture specific and generic HRQOL impact, for example, with questions about limitations in role participation due to a specific disease versus questions about the same limitations without attribution to a specific disease, respectively.

Measures on the left (boxes 1 & 2) are the most specific and, therefore, useful in making a diagnosis and in determining the severity of a specific condition (Patrick D L & Erickson P (1988). Assessing health-related quality of life for clinical decision-making. In Walker S (Ed.), *Quality of life: assessment and application* (pp. 9-49). London: MTP Press; and Deyo R A & Patrick D L (1989). Barriers to the use of health status measures in clinical investigation, patient care, and policy research. *Med. Care*, 27, S254-S268; and Patrick D L & Deyo R A (1989). Generic and disease-specific measures in assessing health status and quality of life. *Med. Care,*. 27, S217-S232, which are incorporated herein by reference in their entirety). In contrast, measures on the right (boxes 3 & 4) are more useful in understanding the impact (on functioning and well-being) of disease and treatment in the more distal HRQOL terms that matter most to patients. In comparison with box 2, measures in box 3 are HRQOL measures because they capture the social and economic impact of disease and treatment. In comparison with box 3, the most generic measures (e.g., Sickness Impact Profile, SF-36 Health Survey) in box 4 are not specific to a disease or treatment and, therefore, permit meaningful comparisons across disease and treatment groups (e.g., (Bergner M, Bobbitt R A, Kressel S, Pollard W E, Gilson B S, & Morris J R (1976). The sickness impact profile: conceptual formulation and methodology for the development of a health status measure. *Int.J Health Serv.*, 6, 393-415; and Stewart A L, Greenfield S, Hays R D, Wells K, Rogers W H, Berry S D et al. (1989). Functional status and well-being of patients with chronic conditions. Results from the Medical Outcomes Study [published erratum appears in JAMA Nov. 10, 1989;262(18):2542]. *JAMA*, 262, 907-913, which are incorporated by reference in their entirety).

As previously conceptualized and measured, the gains in specificity achieved using disease-specific HRQOL measures (box 3) have been achieved at the expense of being able to make meaningful comparisons of burden across diseases and benefit across treatments using those measures. Among the reasons for this lack of comparability are the lack of standardization of domain content and the lack of standardization of scoring algorithms across disease impact metrics. In accordance with an embodiment of the invention, major breakthroughs can be achieved from: (a) standardizing the impact domains sampled to represent HRQOL for purposes of measuring disease-specific outcomes, and (b) standardizing the calibrations used to estimate impact from the same items across diseases (e.g., limited in social activity because of diabetes, limited in social activity because of heart failure).

This conceptual framework of the present invention also makes useful distinctions between the content of measures and helps to illustrate the importance of un-confounding measures across the four boxes. For example, when symptom frequency and/or severity is assessed and scored separately (box 2) and the associated specific impact is assessed and scored separately (box 3), the implications of different symptoms can be meaningfully studied and interpreted in terms of their impact on HRQOL in specific (box 3) or generic (box 4) terms.

In accordance with an embodiment of the present invention, standardizing specific and generic domains as much as possible, both conceptually and in terms of operational definitions, could greatly simplify HRQOL assessment for purposes of clinical trials, everyday clinical practice, health care policy evaluation, and general population monitoring.

The development of the disease impact idea of the present invention builds on three findings: a) when measurement is focused on the impact of a single condition, the impact of that condition on different domains of functional health and well-being (e.g., emotional, social, and role function) is substantially reflected in a single, common dimension of disease impact; b) while diseases differ in severity, the ordering of specific indicators of functional health and well-being is generally the same across disease conditions; and c) by using CAT and IRT it is possible to select questions to match the level of impact experienced by the patient and get a precise estimate of the overall level of impact using only a subset of the available items.

A crucial step in the measurement of any phenomenon is to evaluate dimensionality: How many numbers are needed to adequately describe the phenomenon? Research has established that generic health should be considered multi-dimensional and be described by a profile of scores (Stewart A L & Ware J E, Jr. (1992). *Measuring Functioning and Well-Being: The Medical Outcomes Study Approach*. London: Duke University Press, which is incorporated by reference in its entirety). At most, generic health information can be summarized in two overall components: physical and mental health (Ware J E, Jr., Kosinski M, Bayliss M S, McHorney C A, Rogers W H, & Raczek A (1995). Comparison of methods for the scoring and statistical analysis of SF-36 health profile and summary measures: summary of results from the Medical Outcomes Study. *Med Care*, 33, AS264-79; and Essink-Bot M L, Krabbe P F, Bonsel G J, & Aaronson N K (1997). An empirical comparison of four generic health status measures. The Nottingham Health Profile, the Medical Outcomes Study 36-item Short-Form Health Survey, the COOP/WONCA charts, and the EuroQol instrument. *Med Care*, 35, 522-537, which are incorporated by reference in their entirety). However, when analyzing items on the impact of a specific disease (migraine headache) it was discovered that all items concerning the impact of headache (that is, items specifically mentioning headache) fit a unidimensional measurement model (Bjorner J B, Kosinski M, & Ware J E, Jr. (2003b). The feasibility of applying item response theory to measures of migraine impact: a re-analysis of three clinical studies. *Qual Life Res*, 12, 887-902, which is incorporated by reference in its entirety) even when generic items covering similar concepts fit a multi-dimensional model. The likely reason for this finding is that responses to the generic items are affected by comorbidities. This observation has subsequently been confirmed in independent studies, as discussed herein. (Bjorner J B, Kosinski M, & Ware J E, Jr. (2003c). Using item response theory to calibrate the Headache Impact Test (HIT) to the metric of traditional headache scales. *Qual Life Res*, 12, 981-1002, which is incorporated by reference in its entirety; and Kosinski et al., 2004). In accordance with an embodiment of the present invention, the Computerized Adaptive Testing of Disease Impact (Disease Impact CAT) aims at assessing the disease impact on the following major HRQOL domains: physical, social, role, emotional, and cognitive functioning. A new innovative approach of unifying the disease-specific and generic HRQOL assessment of disease impact is disclosed herein. The Disease Impact CAT of an embodiment of the present invention can produce disease-specific impact scores, which can be comparable on a standard common metric across different diseases.

The basic idea of the disease impact approach of an embodiment of the present invention is illustrated in FIG. 1, which shows the components of disease impact items. A list of functions that may be affected by disease has been established. In a specific assessment of an embodiment of the present invention, a question is asked whether a particular physical, social, role, emotional, or cognitive function is affected by the disease in question.

The measurement properties of each item of an embodiment of the present invention is evaluated through item response theory (van der Linden W J, Hambleton R K. Handbook of Modern Item Response Theory. Berlin: Springer, 1997, which is incorporated by reference in its entirety ) (IRT). IRT is a set of statistical models that describe the probability of choosing a particular item response as a function of item characteristics and the level of disease impact for the particular respondent.

Figure 2B:
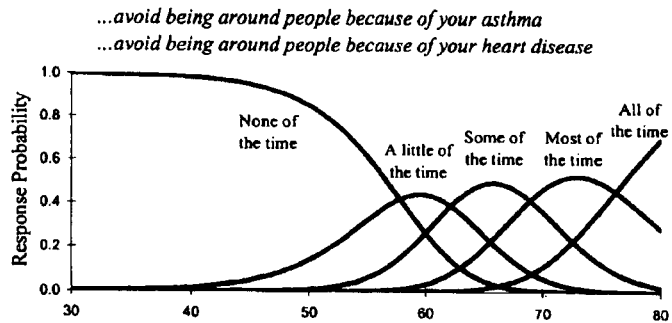
Figure 2C:
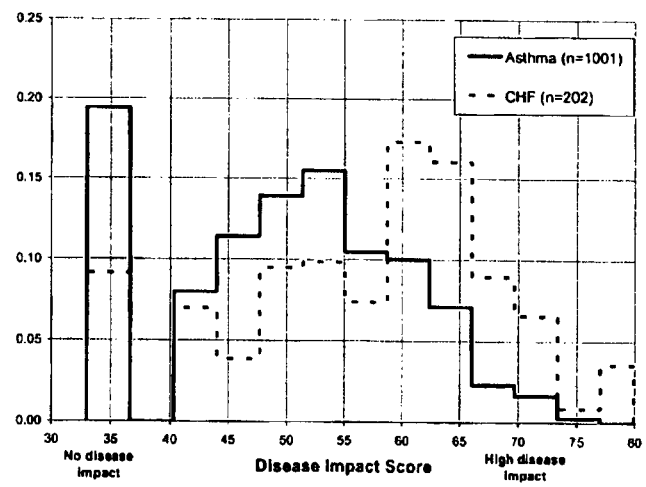

FIGS. 2A-2C demonstrate the IRT model of an embodiment of the present invention for two disease impact items and their relation to the population distribution of disease impact for two diseases. Each line in FIGS. 2A and 2B represent the probability of choosing each item response for a given level of disease impact. The lines in FIGS. 2A and 2B are defined by a set of item parameters that are characteristics of the particular item. These parameters determine the position of the curves along the horizontal axis and the steepness of the curves. In FIG. 2B, the curves for the second item on social avoidance is shifted to the right compared to the first item illustrated in FIG. 2A on irritability, indicating that the second item illustrated in FIG. 2B measures a more severe level of disease impact. Once item parameters have been estimated, it is possible to use the item parameters to estimate the level of disease impact for a particular patient or a group of patients using standard IRT methods (Bock R D. Estimating item parameters and latent ability when responses are scored in two or more nominal categories. *Psychometrika* 1972;37:29-51; Warm T A. Weighted likelihood estimation of ability in item response theory. *Psychometrika* 1989;54:427-50; Mislevy R J. Estimating latent distributions. *Psychometrika* 1984;49:359-81; Mislevy R J. Estimation of Latent Group Effects. *J.Am.Stat.Assoc.* 1985;80:993-7, which are incorporated by reference in their entirety). FIG. 2C illustrates the estimated distribution of disease impact for two diseases: asthma and congestive heart failure (CHF). The columns to the left of FIG. 2C represent people with no measurable impact of their disease in the domains examined. The rest of FIG. 2C illustrates the distribution of impact for people with some impact. On average, CHF has higher impact than asthma, as shown in FIG. 2C. The IRT model used for the analysis of the disease impact items is the Generalized Partial Credit Model (Muraki E. A Generalized Partial Credit Model. In van der Linden W J, Hambleton R K, eds. *Handbook of Modern Item Response Theory*, pp 153-64. Berlin: Springer, 1997, which is incorporated by reference in its entirety).

Figure 3A:
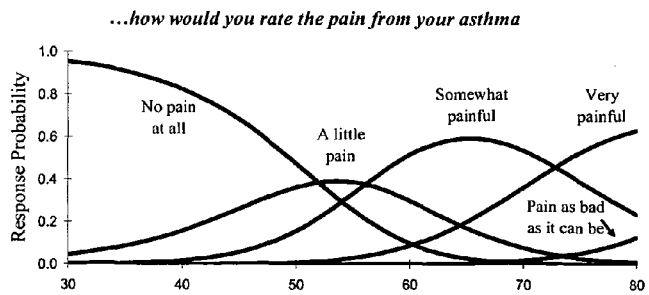
FIGS. 3A-3B depict a series of graphical representations of statistical assessment of two questions and responses thereto as provided by a group of respondents, as well as the graphical representations of a derived statistical assessment of the Assessment Method.
Figure 3B:
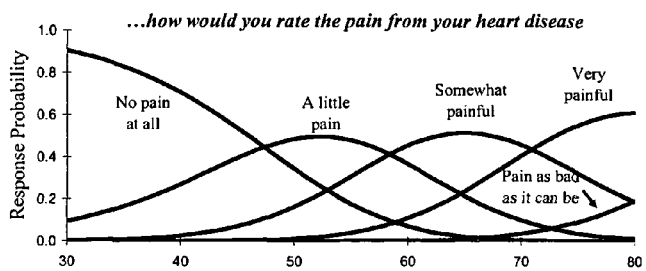

The unique aspect of the disease impact approach of the present invention is the identification of a set of items that has stable item parameters (relative to the other items in the set) across diseases. For example, as shown in FIG. 2A the same model applies for item 1 when used in asthma and in CHF (and likewise for item 2 as shown in FIG. 2B). This means that the probability of selecting a specific response category for a given level of disease impact is the same—regardless of the specific disease. This property of an embodiment of the present invention establishes the common metric that allows for the comparison of disease impact across diseases. The stability of item parameters can be tested through techniques for analysis of differential item functioning (DIF) (Holland P W, Wainer H. Differential item functioning. Hillsdale, N.J.: Lawrence Erlbaum Associates, Inc, 1993, which is incorporated by reference in its entirety). The stability across disease attributions is not a given. FIGS. 3A and 3B illustrate an IRT model of an embodiment of the present invention for an item that did not fulfill the requirement of stability across disease conditions, i.e., an item that was not stable enough to be included in the item bank of an embodiment of the present invention. For a given level of disease impact (as assessed by all other items), patients with CHF tended to give a high rating of pain than people with asthma. Although the difference between curves may seem minor when inspected visually, a statistical test for DIF was highly significant.

To develop the Disease Impact CAT of the present invention, an item bank was built, which can be implemented into the software of the present invention. For building the item bank and constructing a standardized metric of disease impact across different disease groups an item pool of 53 questions, administered via the Internet, was analyzed. Data was collected from N=2,906 subjects suffering from the following five chronic conditions: Asthma (N=1.001), Rhinitis (N=1.001), OsteoArthritis (N=601), Congestive Heart Failure (N=202) and Rheumatoid Arthritis (N=103). Data was collected. All subjects were asked to complete the same 53 disease impact items, but with different disease conditions specified in the item text. Thus, the item text was specific to the disease condition of the particular respondent, i.e., subjects suffering from asthma were asked 'In the past 4 weeks how much of the time did your asthma limit you in performing your usual daily activities . . . ?', whereas subjects suffering from congestive heart failure received the questions 'In the past 4 weeks how much of the time did your heart disease limit you in performing your usual daily activities?'.

The development of the item bank of the present invention involved two data analytic tasks: 1) test that all the disease impact items measure the same underlying concept (i.e., investigate the unidimensionality of the items); 2) evaluate the stability of item parameters, by testing for DIF.

Unidimensionality was evaluated using exploratory and confirmatory factor analyses as described in (Bjorner J B, Kosinski M, Ware J E, Jr. Calibration of an item pool for assessing the burden of headaches: an application of item response theory to the headache impact test (HIT). *Qual Life Res* 2003;12:913-33, which is incorporated by reference in its entirety). Initial data analyses was performed separately for each disease group using factor analytic methods for categorical data (Muthen, B. O. and Muthen, L. Mplus User's Guide. 3(3). 2004. Los Angeles, Muthén & Muthén, which is incorporated by reference in its entirety). Using these approaches a set of items that measures one unidimensional concept of disease impact was established.

The data sets for the five disease groups were combined to investigate DIF across the groups. Investigating DIF was crucial in that the goal was a stable scaling of disease impact items across all disease groups. A stable standardized scaling is achieved, if the estimated item parameters are similar across the disease groups (as was the case for item 1 and for item 2, as shown in FIGS. 2A and 2B, respectively).

In contrast, items showing DIF across disease group (like the item, as shown in FIGS. 3A and 3B) cannot be used to standardize scores across diseases.

The DIF analyses showed that it was possible to identify a set of items with stable item parameter estimates across the disease groups. However, some items that directly reflected the mechanism of only a subset of diseases (e.g., items assessing single disease specific symptoms) functioned differently across diseases and thus had to be excluded. The items meeting the assumption of unidimensionality and showing no meaningful DIF across the disease groups were selected and can form the item bank of the Disease Impact CAT of an embodiment of the present invention. The standardized item parameter estimations of these items can be used by the software of the present invention to guide the item selection of the Disease Impact CAT of the present invention and to enable the disease impact scoring of this new tool of the present invention.

Thus, the disease impact approach of the present invention builds on the new idea that it is possible to identify a set of disease specific items that functions the same way regardless of disease attribution. This hypothesis was tested by investigations of unidimensionality and statistical tests for DIF, and a set of items that functions the same way across different disease groups was established. This item set is used to establish the common disease impact metric of the present invention that allows for the comparison of disease impact across diseases.

EXAMPLE 1

Secondary IRT analyses of data for the SF-36 Health Survey and other questionnaires measuring the same HRQOL concepts was conducted to explore the practical implications of IRT and CAT for clinical research and practice.

Questionnaires self-administered by chronically ill patients (N=2,753) participating in the Medical Outcomes Study (MOS) were reanalyzed (Stewart & Ware, Jr., 1992; Tarlov A R, Ware J E, Jr., Greenfield S, Nelson E C, Perrin E, & Zubkoff M (1989). The Medical Outcomes Study. An application of methods for monitoring the results of medical care. *JAMA*, 262, 925-930, which is incorporated by reference in its entirety). The potential practical implications of IRT models and CAT-based assessments were clearly apparent from analyses where CAT was simulated using real data from people who answered all items in the item bank (Ware J E, Jr., Bjorner J B, & Kosinski M (1999). Dynamic Health Assessment: The Search for More Practical and More Precise Outcome Measures. *Quality of Life Newsletter,* 11-13; and Bjorner J B & Ware J E, Jr. (1998). Using Modem Psychometric Methods to Measure Health Outcomes. *Medical Outcomes Trust Monitor,* 3, 12-16, which are incorporated by reference in their entirety). In such "real data simulations", respondent burden was dramatically reduced for the lowest-scoring patients (bottom third in mental health), for whom the highest standard of precision was set for CAT assessments. Specifically, 92 percent required only five or fewer questionnaire items to satisfy the "clinical" precision standard for an individual patient and the product-moment correlation between full-length (31-item) and dynamic one-minute (five or fewer items) assessments was very high (r=0.985) in the MOS. Cross-sectional tests of the discriminant validity and longitudinal tests of responsiveness were also very favorable for scores estimated dynamically, in comparison with traditional scoring of the full-length questionnaire. Thus, in the MOS, scores estimated using the CAT algorithms were virtually interchangeable with scores based on a static "full-length" form throughout the scale range.

Based on these encouraging preliminary results, studies were conducted to develop item banks for the eight domains represented by the SF-36 Health Survey. Data were collected in samples drawn from the general population using computer interface and telephone interviews. A total of 5,700 questionnaires were administered through the Internet. Those randomly assigned to one of the studies were asked a standard set of demographic questions (age, sex, race/ethnicity, marital status, etc.) plus screening questions to ensure that the sample was representative of the general population. Another 4,800 questionnaires were administered by telephone interview. To obtain a representative sample of respondents, telephone interviewing was conducted using a Random Digit Dialing methodology. For seven banks, items from a variety of commonly used tools were included to allow cross-calibration. For each item bank, a careful psychometric analysis was conducted to identify the best items. The items remaining in the banks have been found to fit a unidimensional IRT model and to be without differential item function for gender, age, education, and race/ethnicity.

EXAMPLE 2

The first fully functioning CAT for medical outcomes was the DYNHA-HIT (Ware J E, Jr., Bjorner J B, & Kosinski M (2000). Practical implications of item response theory and computerized adaptive testing: a brief summary of ongoing studies of widely used headache impact scales. *Med.Care,* 38, II73-II82, which is incorporated by reference in its entirety). This work was initiated by a re-analysis of data from three clinical trials of migraine treatment showing that IRT analysis could successfully be applied to a traditional HRQOL tool (Bjorner et al., 2003b) and that CAT-based scores were as precise or more precise than scores based on traditional tools and methods in evaluating treatment outcome (Kosinski M, Bjorner J B, Ware J E, Jr., Batenhorst A, & Cady R K (2003b). The responsiveness of headache impact scales scored using 'classical' and 'modern' psychometric methods: a re-analysis of three clinical trials. *Qual Life Res,* 12, 903-912, which is incorporated by reference in its entirety). These results prompted development of a CAT-based dynamic headache impact test (DYNHA-HIT). DYNHA-HIT was developed from a new item bank comprised of items from widely-used measures of headache impact. The questionnaires were administered over the telephone by trained interviewers to a national sample of adults suffering from disabling headaches. Data were analyzed using confirmatory factor analysis for categorical data, analysis of differential item functioning, and IRT analyses (Bjorner et al., 2003a). A main finding of these analyses was that all the traditional headache scales were found to measure one unidimensional construct of headache impact, so nearly all items were included in the HIT item pool. Links have been maintained to these source measures, so that all items fitting the IRT model can be calibrated on a common metric and results can be compared across measures. A conversion table has been developed and published to ease comparison of results for these widely-used instruments in relation to DYNHA-HIT, and can be used for the purposes of transferring interpretation guidelines for the dynamic scores back to the metric of scale scores based on traditional summated rating methods (Bjorner et al., 2003c).

To determine whether substantial reductions in respondent burden are possible while maintaining acceptable standards of score precision, simulations of CAT were performed and actual Internet-based CAT administrations among two large samples of recent headache sufferers were evaluated using accepted clinical criteria (Ware, Jr. et al., 2003).

The results strongly suggest that very large reductions in respondent burden (e.g., 90%) are possible using IRT parameters and CAT-based methods of administering HIT items. Further, results from preliminary empirical tests of validity that closely approximate the intended uses of HIT in clinical research suggest that very brief DYNHA-HIT assessments can be programmed to satisfy the precision requirements of both individual patient screening and outcomes monitoring over a wide range of headache impact levels.

As summarized elsewhere (Ware, Jr. et al., 2003), observations of actual CAT assessments of headache-related disability on the Internet suggest that substantial reductions in respondent burden (from 53 full-length items to five or fewer items) are possible, while achieving clinical standards of precision. The widespread interest in DYNHA-HIT since its launch on the Internet demonstrates the feasibility of using Internet-based dynamic assessments to measure health status. The assessments are precise, and brief. Data from 19,000 "real world" takers of DYNHA-HIT confirm results of previous studies by showing DYNHA-HIT to be valid in differentiating respondents on the basis of headache characteristics such as severity and frequency. For example, patients with very high impact scores are very likely to have a disabling headache—such as a cluster headache, severe tension headache or migraine. DYNHA-HIT scores reflect the impact of headache on a person's everyday functioning, using a standard metric so results can be compared. DYNHA-HIT serves as a systematic source of information for clinicians, yields information not always detected by physical examination, and helps monitor populations and/or individuals receiving treatment for headache.

To further enhance the flexibility of headache impact assessment in a variety of settings HIT-6™ was developed. This tool is a fixed-length short form version of DYNHA-HIT for paper and pencil administration with a simplified scoring system intended to match the IRT score as closely as possible (Kosinski M, Bayliss M S, Bjorner J B, Ware J E, Jr., Garber W H, Batenhorst A et al. (2003a). A six-item short-form survey for measuring headache impact: the HIT-6. *Qual Life Res,* 12, 963-974, which is incorporated by reference in its entirety). Construction of the HIT-6 short-form was achieved using the item bank developed for DYNHA-HIT. The tool has been found to be reliable and valid for group-level comparisons, patient-level screening, and to be responsive to changes in headache impact. The HIT-6 items were shown to cover a substantial range of headache impact as defined by the larger item bank and to represent the content areas found in most widely used headache impact tools (Kosinski et al., 2003a). The HIT-6 has been translated for use in 27 countries, which optimizes opportunities for international application and comparability across diverse groups (Gandek, B., Alacoque, J., Uzun, V., Andrew-Hobbs, M., & Davis, K. Translating the Short-Form Headache Impact Test (HIT-6) in 27 Countries: Methodological and Conceptual Issues. *Qual Life Res,* (in press), which is incorporated by reference in its entirety). In conclusion, both the DYNHA-HIT and HIT-6 show excellent criterion validity and responsiveness to change. However, at every score level DYNHA-HIT was more accurate than HIT-6 (Ware, Jr. et al., 2003).

EXAMPLE 3

Figure 5:
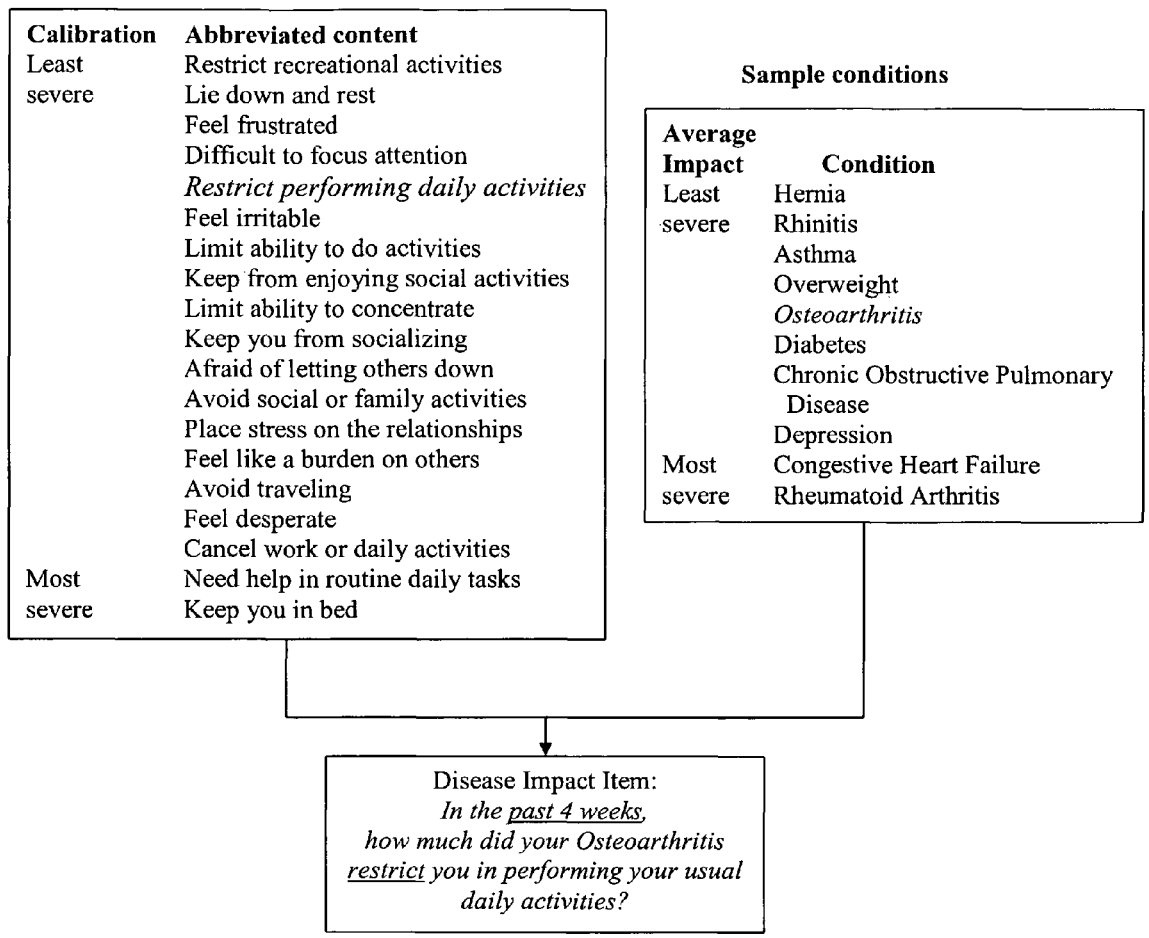
FIG. 5 depicts a flowchart of a further aspect of the Assessment Method.

Based on the results for headache impact as described supra, a study was conducted to investigate whether the scaling of indicators of functional health and well-being impacted by disease would be stable across disease conditions. If the scaling is stable (reflected in stable IRT item parameters across disease groups), the items have the same relative position on a "ruler" of disease impact regardless of disease. In general, this has been the case for the diseases in which the full set of indicators were tested to date: Rhinitis, Asthma, Osteoarthritis, Rheumatoid Arthritis, and Congestive Heart Failure. However, indicators that directly reflected the mechanism of some disease (e.g., questions directly about symptoms) functioned differently for these diseases and were, therefore, excluded. Based on these results, a bank of 37 indicators was constructed with stable scaling over the conditions evaluated. Further, based on responses to a smaller number of items the impact of 43 diseases/conditions were scaled. FIG. 5 illustrates the components of disease impact items of an embodiment of the present invention. FIG. 5 shows examples of indicators of functional health and well-being ordered, on the basis of preliminary IRT calibrations, from least to most severe in terms of the relative level of impact defined by each. FIG. 5 also lists examples of conditions in the order of their relative average impact (from least to most severe). Accordingly, the impact of the more severe conditions (e.g., Congestive Heart Failure) can be most efficiently estimated from indicators assessing the more severe range of the impact continuum in FIG. 5 (e.g., "feel like a burden on others").

In particular, the Disease Impact study, as described supra, was launched to investigate whether the scaling of indicators of disease impact would be stable across disease conditions and if so, to develop a bank of disease impact indicators. Five diseases were investigated: Asthma, Congestive Heart Failure, Osteoarthritis, Rheumatoid Arthritis, and Rhinitis, and data was collected regarding the aforementioned five diseases. Potential participants were asked a standardized set of demographic questions (age, sex, marital status, etc.) plus the screening questions for the study. Participants eligible for this study: (1) were ages 18 years or older; (2) were not employed by any marketing research or advertising company; and (3) screened positive for one of the five conditions. The hypothesis of unidimensionality of the disease impact items was tested using factor analysis for categorical data (Muthen B O & Muthen L (2001). Mplus User's Guide (Version 2) [Computer software]. Los Angeles: Muthén & Muthén, which is incorporated by reference in its entirety) in each of the five disease groups and using multigroup factor analysis for a combined analysis of all groups. The hypothesis of stable scaling of the items across disease groups was further investigated by tests for differential item functioning (DIF) using the logistic regression approach (Zumbo B D (1999). *A handbook on the Theory and Methods of Differential Item Functioning (DIF): Logistic Regression Modeling as a Unitary Framework for Binary and Likert-type (Ordinal) Item Scores*. Ottawa,ON: Directorate of Human Resources Research and Evaluation, Department of National Defense, which is incorporated by reference in its entirety). While most items did not show signs of DIF, a few items did. These indicators directly reflected the mechanism of one of the diseases (e.g., questions directly about symptoms). Based on these results, a bank of 37 indicators was constructed with no DIF across the five disease groups. FIG. 5 shows examples of indicators and conditions and how they combine to form a disease impact item. Based on these items, impact scores could be estimated and compared across the five disease groups (see Table 1).

TABLE 1

Sample size and disease impact score for 5 disease conditions

| Condition | N | Mean[1] | Std. Dev. |
|---|---|---|---|
| Asthma Impact | 1001 | 49.38 | 8.89 |
| Congestive Heart Failure Impact | 202 | 56.76 | 11.91 |
| Osteoarthritis Impact | 601 | 51.61 | 9.82 |
| Rheumatoid Arthritis Impact | 101 | 58.69 | 7.71 |
| Rhinitis Impact | 1001 | 48.45 | 9.61 |

[1]The scale is designed so that the average person with a chronic disease scores 50, and a score of higher than 50 is worse The software of an embodiment of the present invention (described supra) is available through the Internet and as a stand-alone desktop application. The assessment begins with administration of a global item that is selected a priori on the basis of the range it covers. DYNHA's logic for item selection and score estimation builds on item response theory (IRT) and is quite general. However, DYNHA has been optimized for clinical use. Among the important capabilities in this context are: 1) The ability to handle polytomous rank scales items. Among the IRT models handled by DYNHA are the generalized partial credit model, the partial credit model, and the rating scale model; 2) Availability of additional item selection criteria, to ensure the content validity of the assessment. Thus, assessment within a domain can be balanced with regards to subdomains; 3) Immediate feedback to patients and providers, including interpretation guidelines, norm group score benchmarks, and evaluation of patient response consistency, according to the IRT model. Such information is useful to identify potential misreading of questions which can be clarified with the patient immediately after the assessment, in turn leading to improved assessment quality; and 4) Two different ways of IRT scoring: the standard Expected a Posteriori (EAP) scoring (Bock R D & Mislevy R J (1982). Adaptive EAP estimation of ability in a microcomputer environment. *Applied Psychol Measur,* 6, 431-444, which is incorporated by reference in its entirety) and Weighted Maximum Likelihood (WML scoring (Warm T A (1989). Weighted likelihood estimation of ability in item response theory. *Psychometrika,* 54, 427-450, which is incorporated by reference in its entirety).

In accordance with an embodiment of the present invention, a Disease Impact CAT of a comprehensive patient-based system for assessing disease impact that yields user-friendly reports likely to enhance patient-provider communication and improve decision-making can be developed.

In accordance with an embodiment of the present invention software can be programmed to implement the computerized dynamic assessment (DYNHA) of disease impact with a variety of diseases. This new comprehensive assessment can be designed by a team comprised of measurement experts. The clinical partners, who have experience with a dynamic assessment of headache impact, can assist with patient recruitment, participate in the determination of the content and format of the patient and clinician reports, and contribute to the development of practical, useful interpretation guidelines. These guidelines can foster patient-clinician communication, inform treatment decisions, and support individual patient monitoring. Previously collected data can be used to test the stability of item calibrations across age groups and to develop clinical benchmarks for interpretation of the disease impact scores. A User's Acceptance evaluation can be adapted from previous evaluations to assess patient experience completing the instrument, and to gather specific feedback on the reports. The assessment can also include a sociodemographic survey and chronic conditions checklist. A Software Engineering team can program the dynamic assessment system (Disease Impact CAT). Specifically, the overall assessment can be tailored for 'seamless' items administration and report generation. A User's Acceptance survey and chronic conditions checklist can be collected for analysis.

In accordance with an embodiment of the present invention, the present invention can be evaluated on the feasibility of administering the relatively short but comprehensive Disease Impact CAT to middle aged and elderly patients with chronic diseases, evaluate administrative data (e.g., CAT item usage) and evaluate reports that can be printed upon completion of the assessment. The specific objectives of the present invention include: 1) Assessment of respondent burden, range of levels measured, floor and ceiling effects, and item usage; 2) Test of the fit of the IRT model for each respondent through evaluation of response consistency (Drasgow F, Levine M V, & Williams E A (1985). Appropriateness measurement with polychotomous item response models and standardized indices. *Br Journal of Math Stat Psychol,* 38, 67-86, which is incorporated by reference in its entirety) Patients' evaluation of the CAT and the patient feedback report; and 4) Clinicians' evaluation of the usefulness of the clinician feedback report.

In accordance with an embodiment, the results of the present invention can be analyzed, interpreted and summarized.

This approach can allow the Disease Impact CAT of the present invention to be developed and tested, test the user experience of the assessment and the feedback report, and improve the user interface for an additional project.

The evaluation of the equivalence of item calibrations across age groups and the development of clinical benchmarks can be based on previously collected data from the Disease Impact study. Five diseases were investigated: Asthma, Congestive Heart Failure, Osteoarthritis, Rheumatoid Arthritis, and Rhinitis, and data was collected regarding the aforementioned five diseases. Potential participants were asked a standardized set of demographic questions (age, sex, marital status, etc.) plus the screening questions for the study. Participants eligible for this study: (1) were ages 18 years or older; (2) were not employed by any marketing research or advertising company; and (3) screened positive for one of the five conditions. In addition to the disease impact questions, participants received a standard disease-specific questionnaire for their particular disease. These data can be used to develop clinical benchmarks.

For example, a sample of 100 patients 45 years and older with one of the following chronic conditions: Osteoarthritis, Depression, Chronic Obstructive Pulmonary Disease, Diabetes, and Osteoporosis. The disease groups have been selected to include diseases that are common among the elderly and likely represent a large spread in impact. One of the disease groups is included for which the item banks were originally developed and four new diseases to be able to evaluate the consistency and usefulness of the disease impact approach beyond the groups for which it originally was developed. Depression is included, to be able to evaluate the usefulness of the approach for mental health problems. Participants can be sampled from two primary care practices that are part of the Primary Care Network. Patients can be selected to ensure equal representation of the three age groups: 45-59 years, 60-69 years, and 70 years and older. This selection can allow an evaluation and comparison of the feasibility of CAT in different age groups. All participants can be required to speak English as their primary language to avoid prohibitive translation costs.

Protocol can be established that is acceptable by national medical review boards.

Sample participants can be recruited into a study to evaluate the feasibility, efficiency and accuracy of the Disease Impact CAT system of the present invention. They can be asked to complete (a) the dynamic Disease Impact CAT, (b) the static SF-12v2 Health Survey, and (c) a brief post-assessment evaluation. Assessments using the Disease Impact CAT with the DYNHA software can use the Disease Impact item bank and administer the five items that are most informative for each respondent. The SF-12v2 Health Survey can be used to evaluate the relationship between Disease Impact score and generic measures of HRQOL and help to emulate the kind of comprehensive assessment described herein. Data can be entered on a portable computer residing in each clinic. After completion of data collection, data can be analyzed. All data can be handled without any patient personal identifiers.

The Disease Impact CAT of the present invention measures the impact of a specific disease on a person's functioning and well-being. An example of a disease impact item in the context of Osteoarthritis is "In the past 4 weeks, how much of the time has your osteoarthritis interfered with how well you dealt with family, friends, and others who are close to you?" Responses included "none of the time", "a little of the time", "some of the time", "most of the time", and "all of the time". The disease impact item pool currently consists of 37 items. Survey questions are dynamically selected to match each respondent's level of impact and to achieve a pre-set level of score precision or respondent burden. The result is a very brief assessment that meets clinical standards of precision over a very wide range, while substantially (more than 90% for most patients) reducing respondent burden and data collection costs.

User's Acceptance Survey can be constructed to obtain a standardized evaluation of each respondent's experience in completing a comprehensive HRQOL Assessment. As in previous studies (Bayliss et al., 2003) questions can include user's ratings of the overall format and presentation, ease of understanding instructions for administration, survey length, simplicity/clarity of language, number and appropriateness of response choices, feedback report content and layout, relevance, and usefulness in care planning and evaluation.

Other—Respondents can also be asked to complete questions about sociodemographic characteristics and clinical variables used in previous studies (as described above).

These analyses can use data from the Disease Impact Study of the present invention. The following analyses can be performed:

Evaluate the equivalence of item calibrations across age groups. These analyses can evaluate DIF (Holland P W & Wainer H (1993). *Differential item functioning*. Hillsdale, N.J.: Lawrence Erlbaum Associates, Inc, which is incorporated by reference in its entirety) across age groups using logistic regression methods (Swaminathan H & Rogers J H (1990). Detecting Differential Item Functioning Using Logistic Regression Procedures. *J Educ Measur*, 27, 361-370, which is incorporated by reference in its entirety). For large item pools, logistic regression methods are more practical than IRT-based methods. Further, the logistic regression approach allows a fine gradation of age groups, providing more statistical power. DIF is tested by measuring associations between each item and age group, while conditioning on the sum score. Both uniform DIF (differences in threshold parameters) and non-uniform DIF (differences in slope parameters) can be assessed for each item. Items can be considered as exhibiting significant DIF if two criteria are met: statistical significance (p<0.05 after correction for multiple testing) and magnitude of DIF ($R^2$ difference) of at least 2% using Nagelkerke $R^2$ (Nagelkerke N J D (1991). A Note on a General Definition of the Coefficient of Determination," *Biometrika*, 78, 691-692. *Biometrika*, 78, 691-692, which is incorporated by reference in its entirety). If DIF is found, the possibility of correcting for DIF using IRT-based methods can be explored (Thissen D, Steinberg L, & Wainer H (1993). Detection of Differential Item Functioning Using the Parameters of Item Response Models. In Holland P W & Wainer H (Eds.), *Differential Item Functioning* (pp. 67-113). Hillsdale N.J.: Lawrence Erlbaum Ass; and Muraki E (1999). Stepwise Analysis of Differential Item Functioning Based on Multiple-Group Partial Credit Model. *Educ Measur*, 36, 217-232, which are incorporated by reference in their entirety).

*Develop clinical benchmarks for interpretation of disease impact scores*. The benchmarks can be developed directly from the IRT model (see Ware, Jr. et al., 2003) and also from the disease-specific questionnaires administered for Osteoarthritis, for example.

The CAT system of the present invention can be implemented on small portable computers with a touch-screen technology to maximize flexibility in the clinical setting. The assumption that elderly patients will prefer a touch-screen over use of a keyboard or a mouse can be evaluated. A test dataset can be used to evaluate the accuracy of output from the new comprehensive DYNHA software and scores estimated from each specific and generic module, prior to fielding the study.

These reports can contain guidelines for score interpretation. Interpretation guidelines can be based on the typical distribution of impact scores for the particular patient group and on clinical benchmarks developed from the Disease Impact Study data. The clinician report can contain additional technical information (e.g., the precision of the score and the consistency of the patients' responses).

The computerized dynamic health assessment (DYNHA™) software of an embodiment of the present invention that can be used in the tests of dynamically-administered Disease Impact CAT has a number of features that can be evaluated in terms of psychometric performance and user evaluation:

Respondent burden, range of levels measured, floor and ceiling effects, and item usage. The number of items needed for the CAT algorithm to achieve a precise score and the amount of time per administration (in minutes) can be evaluated. Further, the score distribution is evaluated and whether any patients' scores are at the floor or ceiling is tested (lowest and highest possible score). Item usage can be described (number of times each item is administered).

Evaluation of response consistency. The initial evaluation of the stability of item parameters across disease groups relied on tests of differential item functioning. In accordance with an embodiment of the invention, evaluation of response consistency is used (Drasgow et al., 1985) for the same purpose (Custers J W, Hoijtink H, van der N J, & Helders P J (2000). Cultural differences in functional status measurement: analyses of person fit according to the Rasch model. *Qual.Life Res, 9,* 571-578, which is incorporated by reference in its entirety). Such IRT fit methods build on the already established IRT model to generate person-based fit indices. Low response consistency in a particular group suggests that the general IRT model is not appropriate for this disease condition. Since a fit statistic is generated for each person, this methodology can be used with small sample sizes (Custers et al., 2000).

Patients' evaluation of the CAT and the feedback report. Survey feedback regarding the acceptability of the Disease Impact CAT can be examined based on the User's Acceptance Survey.

Clinicians' evaluation of the usefulness of the clinician feedback report. This evaluation can be performed through semi-structured interview with the involved clinicians.

Preliminary evaluations of the feasibility of a Disease Impact CAT of the present invention in clinical settings can be achieved and the analyses can be primarily descriptive (e.g., item usage, number of items required to meet pre-set precision standards, and ratings of acceptance). Evaluation of response consistency can be performed separately for each patient. Thus, the data collected can be adequate to implement the analyses.

Additionally, the general applicability of a comprehensive Disease Impact CAT Assessment System of the present invention standardized across chronic diseases/conditions can be developed and evaluated, in terms of psychometric performance (equivalence across diseases and reliability, validity and precision of scores) and clinical usefulness for randomized trials and everyday practice.

Subjects can be English-speaking adults, ages 45 and older. Non-English speaking subjects might not be included due to costs of translation services. A commitment to the inclusion of a representative sample of participants from minority populations can be made. In following, efforts can be made to recruit a sample that reflects roughly equivalent proportions for gender and race/ethnicity based on the 2000 U.S. population Census estimates for those in the age group 45 years and older (see Table 2).

TABLE 2

Sample Enrollment Table
Study Title: Computerized Adaptive Assessment of Disease Impact - Study
Total Sample Enrollment: 100
SAMPLE ENROLLMENT: Number of Subjects

| | Sex/Gender | | |
|---|---|---|---|
| | Females | Males | Total |
| Ethnic Category | | | |
| Hispanic or Latino | 7 | 6 | 13 |
| Not Hispanic or Latino | 47 | 40 | 87 |
| Ethnic Category Total of All Subjects* | 54 | 46 | 100 |
| Racial Categories | | | |
| American Indian/Alaska Native | 1 | 1 | 2 |
| Asian | 4 | 3 | 7 |
| Native Hawaiian or Other Pacific Islander | 1 | 1 | 2 |
| Black or African American | 7 | 6 | 13 |
| White | 41 | 35 | 76 |
| Racial Categories: Total of All Subjects* | 54 | 46 | 100 |

*The "Ethnic Category Total of All Subjects" must be equal to the "Racial Categories Total of All Subjects."

Sample Enrollment Table (Secondary Analyses)
Study Title: Disease Impact Survey
Total Sample Enrollment: 2,908
SAMPLE ENROLLMENT TABLE (Secondary Analyses): Number of Subjects

| | Sex/Gender | | |
|---|---|---|---|
| | Females | Males | Total |
| Ethnic Category | | | |
| Hispanic or Latino | 53 | 28 | 81 |
| Not Hispanic or Latino | 1932 | 895 | 2,827 |
| Ethnic Category: Total of All Subjects* | 1,985 | 923 | 2,908 |
| Racial Categories | | | |
| American Indian/Alaska Native | 16 | 10 | 26 |
| Asian or Pacific Islander | 40 | 28 | 68 |
| Black or African American | 65 | 19 | 84 |
| White† | 1,746 | 812 | 2,558 |
| Other | 31 | 10 | 41 |
| Preferred not to answer | 87 | 44 | 131 |
| Racial Categories: Total of All Subjects* | 1,985 | 923 | 2,908 |

*The "Ethnic Category Total of All Subjects" must be equal to the "Racial Categories Total of All Subjects."

Subjects can be asked to complete a survey intended to assess the impact of their disease on their daily life and a post-assessment evaluation. The exclusion criterion can be any respondent that does not speak English as a primary language or is unable to answer questionnaires due to cognitive limitations. Subjects participating in this study can not undergo any physical testing.

The risks of participation in this study are very minimal. There is no treatment or physical testing beyond the standard clinical procedures involved.

The Nurse/Study Coordinator can identify patients through the clinic sites at the Primary Care Network who meet eligibility criteria. Patients can be asked to participate in the study by their clinicians and those who indicate an interest can be asked to meet with the Nurse/Study Coordinator, who can explain the study and present the consent information in writing and verbally. The assessment can be conducted by the Nurse/Study Coordinator, who can obtain signed consent prior to survey administration. The Nurse/Study Coordinator can take into account and record any participant-reported physical and cognitive limitations and use of assistive devices. At the meeting, the Nurse/Study Coordinator can review the consent information, obtain a signed consent form, and administer the instrument.

Data from the computerized assessment can be uploaded from the local computer. The clinic site can use only code number identification in the data set or on the paper questionnaires. The key linking code numbers to identifying information can be kept by the local site clinical coordinator. Study data can be maintained in secure computers meeting data security standards, including those set forth in Privacy Rule of the Health Insurance Portability and Accountability Act (HIPAA) of 1996, the Security Rule of HIPAA, and all other relevant laws and regulations. Protected Health Information (PHI) for patients may not be released from the Primary Care Network clinic sites. PHI can only be needed to identify members for project enrollment. During this period, all PHI related data can be stored on secure networks and password protected at the Primary Care Network clinic sites. Data stored on certain proprietary websites can contain no PHI related data, only a study identifier. Because this is a member-based survey asking about perceptions of health, significant risks to subjects from completing the survey is not anticipated. To reduce risks to subjects, validated instruments that have been used in previous research, approved by external Institutional Review Boards are used.

All participating personnel in this proposal have either already completed human subjects training, or can complete Human Participant Protections: Education for Research Teams by the National Institutes of Health.

The benefit to risk ratio is very high, given the extremely low level of risk involved and the value of the information to be gained. Individual subjects may benefit from participating in the study in that (a) their unique perspective on their HRQOL is being considered and integrated into their disease management, and/or (b) they feel a sense of satisfaction in contributing to an important project that can lead to improved outcomes measurement. In addition, patients can be provided with a financial incentive for their participation in the study.

Risks to participants are very low in relation to benefit gained through participation in a study that provides a direct comprehensive health status assessment. This may serve as an opportunity for some subjects to feel empowered in that by participating, they are furthering the field of disease impact assessment and contributing to improving clinician-patient communication.

The sample is intended to be representative of the population 45 years and older. With regard to inclusion of women, the full spectrum of representation is sought, and targeted enrollment can be based on 2000 U.S. Census data for gender distribution among those 45 years and older.

The sample is intended to be representative of the population 45 years and older. With regard to inclusion of minorities, the full spectrum of representation is sought, and targeted enrollment can be based on 2000 U.S. Census data for race/ethnicity distribution among those 45 years and older. Participation of racial/ethnic subgroups is sought to be maximized, and the study can be conducted at an additional site in order to achieve the enrollment targets.

Issues applicable to the study of HRQOL and other relevant topics for children differ from those that are relevant to adults in this population. The assessment system used in this project is designed for adult patients with chronic conditions. CAT for the pediatric population in other company projects is being addressed.

While specific embodiments of the invention have been shown and described in detail to illustrate the invention, it will be understood that the invention may be embodied otherwise without departing from the principles of the invention and that various modifications, alternate constructions, and equivalents will occur to those skilled in the art given the benefit of this disclosure, Thus, the invention is not limited to the specific embodiment described herein, but is defined by the appended claims.

What is claimed:

1. A computer based system for assessing the impact of an ailment on a health related quality of life (HRQOL) domain of a patient, wherein said HRQOL domain comprises a plurality of indicators of functional health and well being, comprising:
    a microprocessor configured to:
        generate a customized test having a plurality of questions for said patient to determine the impact of said ailment on said HRQOL domain, wherein each question comprises an indicator of functional health and well being as a result of said ailment, wherein said indicator is stably scaled across ailments whose impact is to be assessed to establish a standardized common metric for comparing the impact of various ailments;
        administer said test by providing one question at a time to said patient;
        evaluate, after each question, answers provided by said patient to estimate an ailment impact score and a confidence level in the accuracy of said estimated ailment impact score;
        vary a threshold, after each question, as a function of said estimated aliment impact score during administration of said test to said patient; and
        dynamically modify said test if said estimated confidence level is outside said threshold;
    an interface associated with said microprocessor to present said test to said patient and to receive said answers provided by said patient; and
    a database associated with said processor to store said test, said plurality of questions, said answers provided by said patient, and said estimated ailment impact score.

2. The system of claim 1, wherein said microprocessor provides a list of possible answers for each question from said database to said patient via said interface.

3. The system of claim 1, wherein said microprocessor generates said test to determine the impact of said ailment on a condition experienced or perceived by said patient, said condition being physical, social, role, emotional, and cognitive functioning.

4. The system of claim 1, wherein said microprocessor generates said test to determine the impact of said ailment on at least one of the following indicators of functional health and well being: restrict recreational activities, lie down and rest, feel frustrated, difficult to focus attention, restrict performing daily activities, feel irritable, limit ability to do activities, difficulty in performing daily activities, keep from enjoying social activities, limit ability to concentrate, keep you from socializing, afraid of letting others down, avoid social or family activities, place stress on your relationships, feel like a burden on others, avoid traveling, feel desperate, cancel work or daily activities, need help in routine daily tasks, and keep you in bed.

5. The system of claim 1, wherein said microprocessor generates said test to determine the impact of one of the following ailments: headache, hernia, rhinitis, asthma, overweight, osteoarthritis, diabetes, chronic obstructive pulmonary disease, depression, congestive heart failure, and rheumatoid arthritis.

6. The system of claim 1, wherein said microprocessor is further configured to generate a report regarding said estimated ailment impact score of said patient, and to compare said answers provided by said patient with answers provided by other patients in said domain stored in said database.

7. The system of claim 1, wherein said microprocessor is further configured to rank said plurality of questions in accordance with said estimated ailment impact score, and to select a highest ranked question that has not been administered to said patient from said plurality of questions stored in said database based on said ranking.

8. The system of claim 1, wherein said microprocessor is further configured to terminate said administration of said test if it is determined that said estimated confidence level is within said threshold.

9. The system of claim 1, wherein said microprocessor generates said test having said plurality of questions to determine the impact of said ailment on a plurality of HRQOL domains.

10. The system of claim 1, wherein said microprocessor is configured to statistically analyze said answers provided by said patient for errors, consistency, or estimating non-responsive answers to said test.

11. The system of claim 1, further comprising a network and wherein said microprocessor is configured to administer said customized test to said patient over said network.

12. The system of claim 1, wherein said microprocessor is configured to generate said standardized common metric of the impact of an ailment on said HRQOL domain across a plurality of ailments or age groups.

13. The system of claim 12, wherein said microprocessor is further configured to:
perform a uni-dimensionality evaluation on a plurality of indicators of functional health and well-being impacted by said plurality of ailments to provide a first set of candidate indicators;
perform a differential item functioning analyses on said plurality of indicators of functional health and well-being impacted by said plurality of ailments to provide a second set of candidate indicators;
build an item bank of said plurality of indicators of functional health and well-being impacted by said plurality of ailments from said indicators that are members of both said first and second sets of candidate indicators to provide indicators that are stably scaled across said plurality of ailments or age groups; and
order said indicators of functional health and well-being impacted by said plurality of ailments that are stably scaled across said plurality of ailments or age groups in accordance with the relative level of ailment impact defined by each to form said standardized common metric of the impact of an ailment on said HRQOL domain of said at least one patient across said plurality of ailments or age groups.

14. The system of claim 1, wherein said microprocessor is further configured to develop clinical benchmarks for interpretation of said estimated ailment impact score.

15. A method of assessing the impact of an ailment on a health related quality of life (HRQOL) domain of a patient, wherein said HRQOL domain comprises a plurality of indicators of functional health and well being, comprising the steps of:
generating a customized test from a database comprising questions for a plurality of HRQOL domains, said test having a plurality of questions for said patient to determine the impact of said ailment on said HRQOL domain by a microprocessor, wherein each question comprises an indicator of functional health and well being as a result of said ailment, wherein said indicator is stably scaled across ailments whose impact is to be assessed to establish a standardized common metric for comparing the impact of various ailments;
administering said test by said microprocessor by providing one question at a time to said patient via an interface associated with said microprocessor;
evaluating by said microprocessor, after each question, answers provided by said patient to estimate an ailment impact score and a confidence level in the accuracy of said estimated ailment impact score;
varying a threshold by said microprocessor, after each question, as a function of said estimated aliment impact score during administration of said test to said patient;
storing said test, said answers provided by said patient, and said estimated ailment impact score in said database; and
dynamically modifying said test by said microprocessor if said estimated confidence level is outside said threshold.

16. The method of claim 15, further comprising the step of providing a list of possible answers for each question by said microprocessor from said database to said patient via said interface.

17. The method of claim 15, further comprising the step of generating said test by said microprocessor to determine the impact of said ailment on a condition experienced or perceived by said patient, said condition being at least one of the following: physical, social, role, emotional, and cognitive functioning.

18. The method of claim 15, further comprising the step of generating said test by said microprocessor to determine the impact of said ailment on at least one of the following indicator of functional health and well being: restrict recreational activities, lie down and rest, feel frustrated, difficult to focus attention, restrict performing daily activities, feel irritable, limit ability to do activities, difficulty in performing daily activities, keep from enjoying social activities, limit ability to concentrate, keep you from socializing, afraid of letting others down, avoid social or family activities, place stress on your relationships, feel like a burden on others, avoid traveling, feel desperate, cancel work or daily activities, need help in routine daily tasks, and keep you in bed.

19. The method of claim 15, further comprising the step of generating said test by said microprocessor to determine the impact of one of the following ailments on said patient: headache, hernia, rhinitis, asthma, overweight, osteoarthritis, diabetes, chronic obstructive pulmonary disease, depression, congestive heart failure, and rheumatoid arthritis.

20. The method of claim 15, further comprising the steps of generating by said microprocessor a report regarding said estimated ailment impact score of said patient and comparing by said microprocessor said answers provided by said patient with answers provided by other patients in said domain stored in said database.

21. The method of claim 15, further comprising the steps of ranking said plurality of questions by said microprocessor in accordance with said estimated ailment impact score; selecting a higher ranked question by said microprocessor that has not been administered to said patient from said plurality of questions stored in said database based on said ranking.

22. The method of claim 15, further comprising the step of terminating said administration of said test by said microprocessor if it is determined that said estimated confidence level is within said threshold.

23. The method of claim 15, further comprising the step of generating by said microprocessor said test having said plurality of questions to determine the impact of said ailment on a plurality of HRQOL domains.

24. The method of claim 15, further comprising the step of statistically analyzing by said microprocessor said answers provided by said patient for errors, consistency, or estimating non-responsive answers to said test.

25. The method of claim 22, further comprising the step of administering by said microprocessor said test to said patients over a network.

26. The method of claim 15, further comprising the step of generating by said microprocessor said standardized common metric of the impact of an ailment on said HRQOL domain across a plurality of ailments or age groups.

27. The method of claim 15, further comprising the steps of:
  performing by said microprocessor a uni-dimensionality evaluation on a plurality of indicators of functional health and well-being impacted by said plurality of ailments to provide a first set of candidate indicators;
  performing by said microprocessor a differential item functioning analyses on said plurality of indicators of functional health and well-being impacted by said plurality of ailments to provide a second set of candidate indicators;
  building by said microprocessor an item bank of said plurality of indicators of functional health and well-being impacted by said plurality of ailments from said indicators that are members of both said first and second sets of candidate indicators to provide indicators that are stably scaled across said plurality of ailments or age groups; and
  ordering by said microprocessor said indicators of functional health and well-being impacted by said plurality of ailments that are stably scaled across said plurality of ailments or age groups in accordance with the relative level of ailment impact defined by each to form said standardized common metric of the impact of an ailment on said HRQOL domain of said at least one patient across said plurality of ailments or age groups.

28. The method of claim 15, further comprising the step of developing by said microprocessor clinical benchmarks for interpretation of said estimated ailment impact score.

29. A computer readable medium comprising code for assessing the impact of an ailment on a health related quality of life (HRQOL) domain of a patient, wherein said HRQOL domain comprises a plurality of indicators of functional health and well being, said code comprising computer executable instructions for:
  generating a customized test having a plurality of questions for said patient to determine the impact of said ailment on said HRQOL domain, wherein each question comprises an indicator of functional health and well being as a result of said ailment, wherein said indicator is stably scaled across ailments whose impact is to be assessed to establish a standardized common metric for comparing the impact of various ailments;
  administering said test by providing one question at a time to said patient;
  evaluating, after each question, answers provided by said patient to estimate an ailment impact score and a confidence level in the accuracy of said estimated ailment impact score;
  varying a threshold, after each question, as a function of said estimated aliment impact score during administration of said test to said patient;
  storing said test, said answers provided by said patient, and said estimated ailment impact score in a database; and
  dynamically modifying said test said estimated confidence level is outside said threshold.

30. The computer readable medium of claim 29, further comprising computer executable instructions for terminating said administration of said test if it is determined that said estimated confidence level is within said threshold.

31. The computer readable medium of claim 29, further comprising computer executable instructions for statistically analyzing said answers provided by said patient for errors, consistency, or estimating non-responsive answers to said test.

* * * * *

UNITED STATES PATENT AND TRADEMARK OFFICE
CERTIFICATE OF CORRECTION

Page 1 of 1

PATENT NO. : 7,818,185 B2
APPLICATION NO. : 11/377773
DATED : October 19, 2010
INVENTOR(S) : Jakob B. Bjorner et al.

It is certified that error appears in the above-identified patent and that said Letters Patent is hereby corrected as shown below:

In title page, item (*) Notice, insert --This patent is subject to a terminal disclaimer.--.

In claim 29, column 40, line 33, delete "test said" and insert --test if said-- therefor.

Signed and Sealed this
Fifteenth Day of February, 2011

David J. Kappos
*Director of the United States Patent and Trademark Office*